(12) United States Patent
Caffrey et al.

(10) Patent No.: US 9,689,814 B2
(45) Date of Patent: Jun. 27, 2017

(54) CHEMICAL DETECTION SYSTEM AND RELATED METHODS

(71) Applicant: Battelle Energy Alliance, LLC, Idaho Falls, ID (US)

(72) Inventors: Augustine J. Caffrey, Idaho Falls, ID (US); David L. Chichester, Idaho Falls, ID (US); Ann E. Egger, Pocatello, ID (US); Kenneth M. Krebs, Idaho Falls, ID (US); Edward H. Seabury, Idaho Falls, ID (US); Clinton D. Van Siclen, Idaho Falls, ID (US); C. Jayson Wharton, Idaho Falls, ID (US); John M. Zabriskie, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 550 days.

(21) Appl. No.: 13/847,266

(22) Filed: Mar. 19, 2013

(65) Prior Publication Data

US 2014/0284490 A1    Sep. 25, 2014

(51) Int. Cl.
G01N 23/222 (2006.01)

(52) U.S. Cl.
CPC .................. *G01N 23/222* (2013.01)

(58) Field of Classification Search
CPC ....... G01T 3/00; G01N 23/222; G01N 24/084
USPC ................ 250/390.01, 390.04, 393
See application file for complete search history.

(56) References Cited

U.S. PATENT DOCUMENTS

| 3,778,627 | A | * | 12/1973 | Carpenter ..................... 376/192 |
| 4,882,121 | A | * | 11/1989 | Grenier ......................... 376/159 |
| 5,162,096 | A | * | 11/1992 | Gozani .......................... 376/159 |
| 5,200,626 | A | * | 4/1993 | Schultz et al. ............ 250/390.04 |
| 5,378,895 | A | * | 1/1995 | Cole et al. ................ 250/390.04 |
| 5,552,608 | A | * | 9/1996 | Gallagher et al. ....... 250/370.15 |

(Continued)

OTHER PUBLICATIONS

Caffrey et al., "Chemical Warfare Agent and Explosive Identification by Spectroscopy of Neutron-Induced Gamma Rays," IEEE Transactions on Nuclear Science, vol. 39, No. 5 (Oct. 1992) 1422-1426.

(Continued)

*Primary Examiner* — David Porta
*Assistant Examiner* — Djura Malevic
(74) *Attorney, Agent, or Firm* — TraskBritt

(57) ABSTRACT

A chemical detection system includes a frame, an emitter coupled to the frame, and a detector coupled to the frame proximate the emitter. The system also includes a shielding system coupled to the frame and positioned at least partially between the emitter and the detector, wherein the frame positions a sensing surface of the detector in a direction substantially parallel to a plane extending along a front portion of the frame. A method of analyzing composition of a suspect object includes directing neutrons at the object, detecting gamma rays emitted from the object, and communicating spectrometer information regarding the gamma rays. The method also includes presenting a GUI to a user with a dynamic status of an ongoing neutron spectroscopy process. The dynamic status includes a present confidence for a plurality of compounds being present in the suspect object responsive to changes in the spectrometer information during the ongoing process.

26 Claims, 22 Drawing Sheets

(56) References Cited

U.S. PATENT DOCUMENTS

| | | | |
|---|---|---|---|
| 5,811,816 A * | 9/1998 | Gallagher et al. | 250/370.15 |
| 5,838,759 A * | 11/1998 | Armistead | 378/57 |
| 6,393,085 B1 * | 5/2002 | Heller et al. | 376/158 |
| 6,668,033 B1 * | 12/2003 | Schelten | 376/159 |
| 6,791,089 B1 * | 9/2004 | Caffrey et al. | 250/358.1 |
| 7,041,508 B2 * | 5/2006 | Smith | 436/104 |
| 7,285,784 B2 * | 10/2007 | Rowland et al. | 250/370.15 |
| 7,307,256 B1 * | 12/2007 | Reber et al. | 250/339.07 |
| 7,505,544 B2 * | 3/2009 | Jestice | 376/159 |
| 7,514,695 B2 * | 4/2009 | Caffrey | 250/393 |
| 7,573,044 B2 * | 8/2009 | Norris | 250/390.04 |
| 7,663,119 B2 * | 2/2010 | Sved | 250/390.01 |
| 7,778,783 B2 * | 8/2010 | Lingren et al. | 702/28 |
| 7,783,004 B2 * | 8/2010 | Kotowski et al. | 378/57 |
| 7,795,595 B2 * | 9/2010 | Reber et al. | 250/390.01 |
| 8,080,808 B2 * | 12/2011 | Norris | 250/390.04 |
| 8,217,360 B2 * | 7/2012 | Nukatsuka et al. | 250/370.11 |
| 8,275,091 B2 * | 9/2012 | Morton et al. | 378/57 |
| 8,304,740 B1 * | 11/2012 | Frank | 250/370.11 |
| 8,358,731 B2 * | 1/2013 | Jestice | 376/159 |
| 8,410,451 B2 * | 4/2013 | Norris | 250/393 |
| 8,748,837 B2 * | 6/2014 | Carasco et al. | 250/389 |
| 2003/0165212 A1 * | 9/2003 | Maglich | 376/156 |
| 2005/0135536 A1 * | 6/2005 | Lyoussi et al. | 376/159 |
| 2007/0290133 A1 * | 12/2007 | Reber et al. | 250/339.07 |
| 2008/0017806 A1 * | 1/2008 | Norris | 250/390.04 |
| 2008/0092556 A1 * | 4/2008 | Stein et al. | 62/45.1 |
| 2008/0123808 A1 * | 5/2008 | Caffrey | 378/57 |
| 2009/0001286 A1 * | 1/2009 | Kearfott | 250/484.2 |
| 2010/0148084 A1 * | 6/2010 | Sved | 250/390.04 |
| 2011/0155920 A1 * | 6/2011 | Hupont et al. | 250/393 |
| 2011/0233419 A1 * | 9/2011 | Norris | 250/390.04 |
| 2012/0037812 A1 * | 2/2012 | Norris | 250/393 |
| 2012/0183111 A1 * | 7/2012 | Yea et al. | 376/159 |
| 2012/0199753 A1 * | 8/2012 | Chuang et al. | 250/390.04 |
| 2014/0100878 A1 * | 4/2014 | Adams | G06F 19/321 705/3 |

OTHER PUBLICATIONS

Caffrey et al., "A DD Neutron Generator-Based PGNAA System for Chemical Warfare Agent and Explosives Identification," Poster Presented at the IEEE Nuclear Science Symposium, Knoxville, TN, Oct. 30-Nov. 6, 2010.

Ortec, "Trans-SPEC and trans-SPEC-100" 2007, 8 pages.

Ortec, "trans-SPEC-DX-100T" 2013, 8 pages.

Seabury et al., "Explosive Detection and Identification by PGNAA," Idaho National Engineering and Environmental Laboratory, Nov. 2004, 30 pages.

Seabury et al., "Explosive Detection and Identification by PGNAA," Idaho National Laboratory, Apr. 2006, 21 pages.

Seabury et al., "PINS Measurements of Explosive Simulants for Cargo Screening," Idaho National Laboratory, Jun. 2008, 42 pages.

Seabury et al., "PINS Testing and Modification for Explosive Identification," INL/EXT-11-23378, dated Feb. 28, 2012, 29 pages.

* cited by examiner (b) Poor resolution, index = 52%

(a) Good resolution, index = 96%

CHEMICAL DETECTION SYSTEM AND RELATED METHODS

STATEMENT REGARDING FEDERALLY SPONSORED RESEARCH OR DEVELOPMENT

This disclosure was made with government support under Contract No. DE-AC07-051D14517 awarded by the United States Department of Energy. The government has certain rights in the disclosure.

TECHNICAL FIELD

Embodiments of the present disclosure are directed to methods, systems, and apparatus for the non-destructive identification of chemicals using prompt gamma-ray neutron activation analysis. More particularly, the embodiments of the present disclosure relate to non-destructive methods, systems, and apparatus for testing and identifying one or more chemicals of interest, such as chemical warfare agents and reactive or explosive materials, utilizing a portable, field deployable, neutron generator and particle detector.

BACKGROUND

The United States military has used neutron activation analysis techniques known as portable isotopic neutron spectroscopy ("PINS") system for non-destructive identification of suspect chemical munitions and containers for the past several years. The PINS system employs neutron radiation to probe the chemical elements within sealed munitions or containers. The PINS assay begins with obtaining an uncalibrated, raw gamma-ray spectra from a portable high-purity germanium gamma-ray spectrometer. The process of obtaining or generating the gamma-ray spectra is usually performed in the field (e.g., at a munitions disposal site). The gamma-ray spectra are calibrated and analyzed in the field by the PINS software. These gamma-ray spectra are then sent to a nuclear laboratory for expert interpretation to identify the contents of the container or munitions or may be performed on-site.

One example of a PINS chemical identification system is disclosed in U.S. Pat. No. 6,791,089. As disclosed therein, a system including a neutron source including californium-252 may be emitted toward an object to be tested. The resultant gamma rays are detected by a high purity germanium detector (HPGe), which is placed at an angle relative to the neutron source. The resultant gamma rays are then analyzed by the software system disclosed therein.

BRIEF SUMMARY

Embodiments of the present disclosure include a chemical detection system including a frame, an emitter coupled to the frame, and a detector coupled to the frame proximate the emitter. The chemical detection system also includes a shielding system coupled to the frame and positioned at least partially between the emitter and the detector, wherein the frame positions a sensing surface of the detector in a direction substantially parallel to a plane extending along a front portion of the frame.

Embodiments of the present disclosure include a method of detecting a chemical makeup of an object with a portable chemical detection system. The method includes emitting neutrons at the object with a neutron emitter of the portable chemical detection system. The method also includes detecting radiation generated by the object responsive to excitation of at least a portion of the object by the neutrons from the neutron emitter with a detector of the portable chemical detection system and moving the portable chemical detection system along at least a portion of the object.

Embodiments of the present disclosure include a chemical analysis system including a neutron generator configured for directing neutrons at a suspect object and a gamma-ray spectrometer configured for detecting gamma rays emitted from the suspect object and communicating spectrometer information regarding the detected gamma rays. A computing system is configured for operable communication with the gamma-ray spectrometer to receive the spectrometer information. The computing system includes a memory configured for storing computing instructions and a processor operably coupled to the memory and configured for executing the computing instructions to present a Graphical User Interface (GUI) with dynamic status of an ongoing neutron spectroscopy process, wherein the dynamic status includes a present confidence for a plurality of compounds being present in the suspect object.

Embodiments of the present disclosure include a method of analyzing composition of a suspect object. The method includes directing neutrons at a suspect object, detecting gamma rays emitted from the suspect object, and communicating spectrometer information regarding the detected gamma rays. The method also includes presenting a GUI to a user, the GUI including a dynamic status of an ongoing neutron spectroscopy process, wherein the dynamic status includes a present confidence for a plurality of compounds being present in the suspect object responsive to changes in the spectrometer information during the ongoing process.

BRIEF DESCRIPTION OF THE DRAWINGS

While the specification concludes with claims particularly pointing out and distinctly claiming that regarded as embodiments of the present disclosure, the advantages of embodiments of the disclosure may be more readily ascertained from the following description of embodiments of the disclosure when read in conjunction with the accompanying drawings in which:

DETAILED DESCRIPTION

Figure 1:
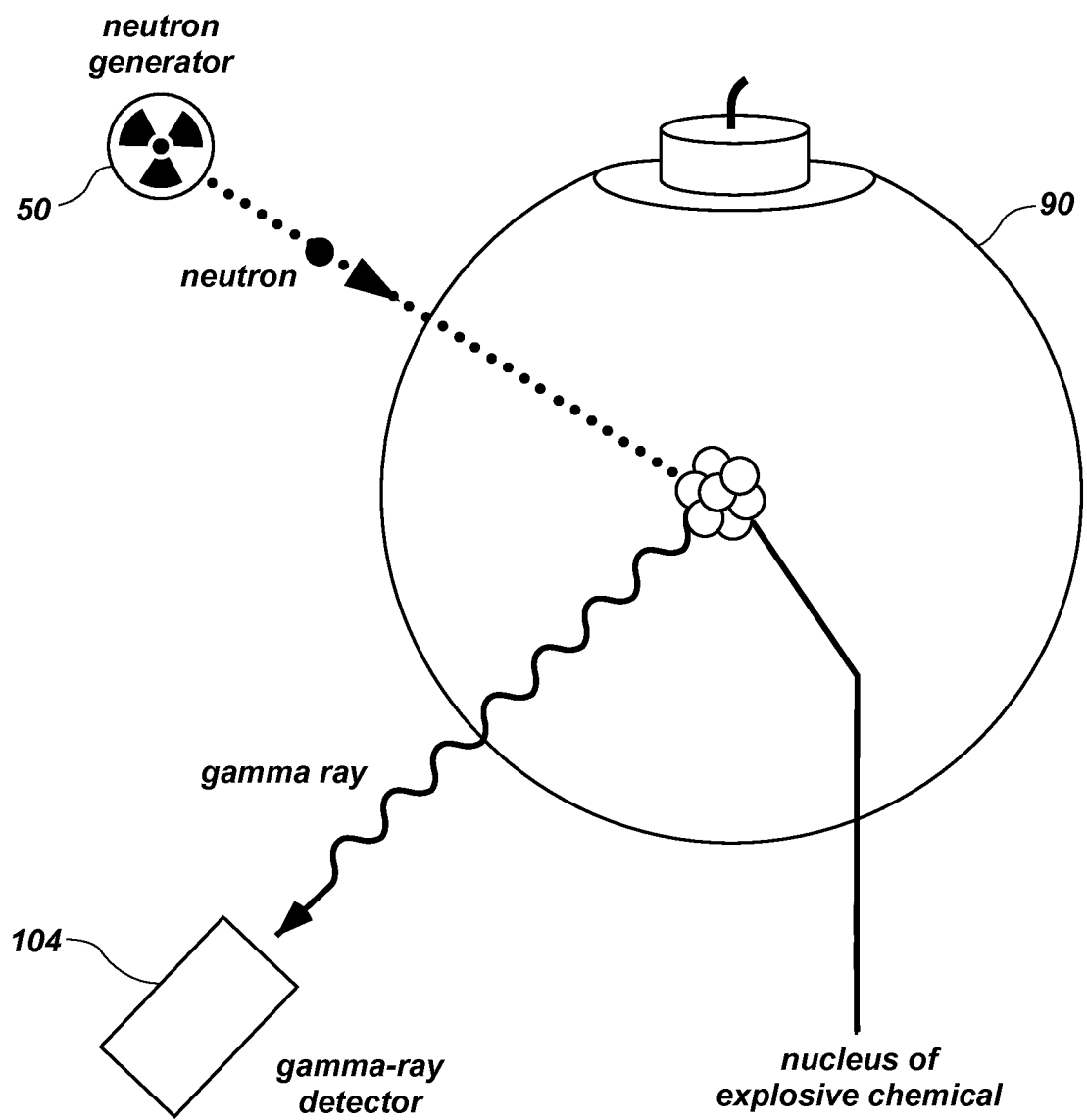
FIG. 1 is an overview diagram illustrating some elements of nuclear spectroscopy.

The illustrations presented herein are not meant to be actual views of any particular material, device, apparatus, assembly, system, or method, but are merely idealized representations that are employed to describe embodiments of the present disclosure. Additionally, elements common between figures may retain the same numerical designation for convenience and clarity.

Furthermore, specific implementations shown and described are only examples and should not be construed as the only way to implement or partition the present disclosure into functional elements unless specified otherwise herein. It will be readily apparent to one of ordinary skill in the art that the various embodiments of the present disclosure may be practiced by numerous other partitioning solutions.

In the following description, elements, circuits, and functions may be shown in block diagram form in order not to obscure the present disclosure in unnecessary detail. Additionally, block definitions and partitioning of logic between various blocks is exemplary of a specific implementation. It will be readily apparent to one of ordinary skill in the art that the present disclosure may be practiced by numerous other partitioning solutions. Those of ordinary skill in the art would understand that information and signals may be represented using any of a variety of different technologies and techniques. For example, data, instructions, commands, information, signals, bits, symbols, and chips that may be referenced throughout the description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths and the present disclosure may be implemented on any number of data signals including a single data signal.

The various illustrative logical blocks, modules, and circuits described in connection with the embodiments disclosed herein may be implemented or performed with a general-purpose processor, a special-purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A general-purpose processor may be considered a special-purpose processor while the general-purpose processor is configured to execute instructions (e.g., software code) stored on a computer-readable medium. A processor may also be implemented as a combination of computing devices, such as a combination of a DSP and a microprocessor, a plurality of microprocessors, one or more microprocessors in conjunction with a DSP core, or any other such configuration.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed or that the first element must precede the second element in some manner. In addition, unless stated otherwise, a set of elements may comprise one or more elements.

FIG. 1 is on overview diagram illustrating some elements of neutron spectroscopy. A Portable Isotopic Neutron Spectroscopy (PINS) Explosive Identification System identifies explosive compounds and mixtures nondestructively, providing significant safety benefits. As shown in FIG. 1, PINS probes an item under test 90 (may also be referred to herein as a suspect object) with neutrons emitted by a neutron generator 50. The neutrons excite the atomic nuclei of substances within the item under test 90, producing characteristic gamma rays. The gamma rays are detected by a gamma-ray detector 104. The energy-intensity pattern (i.e., spectrum) of these gamma rays is unique for each chemical element, and by analyzing the gamma-ray spectrum, the PINS software can identify the chemical elements inside the item under test 90 and with analysis of the various chemical elements the PINS software can determine if various types of explosives are present. PINS can often identify the type of explosive as well.

Figure 2:
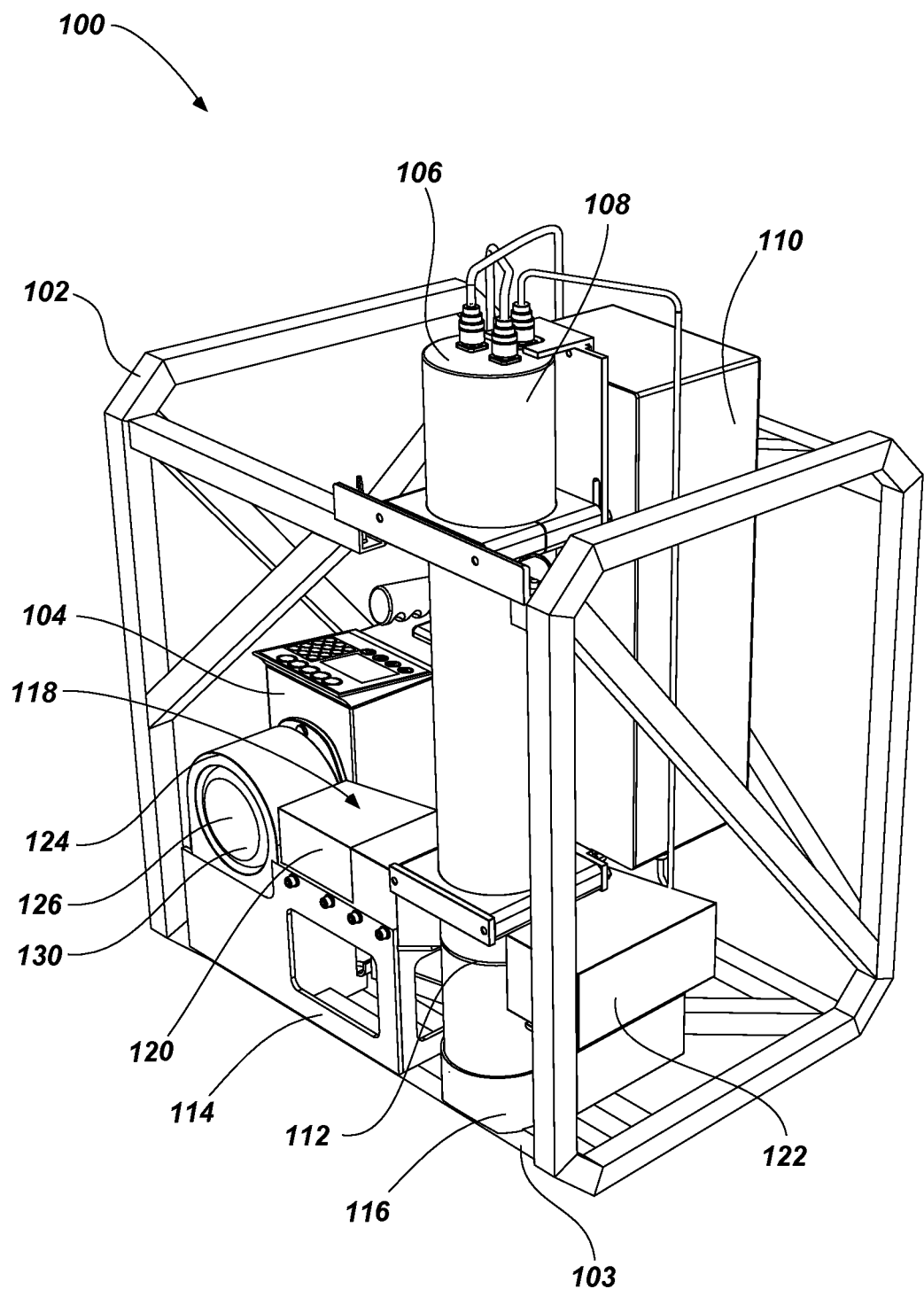
FIG. 2 is a perspective view of a chemical detection system in accordance with an embodiment of the present disclosure.

FIG. 2 illustrates a perspective view of a chemical detection system 100. The chemical detection system 100 includes a frame 102 to which each of the components of the chemical detection system 100 may be mounted. For example, the chemical detection system 100 includes a detector 104 (e.g., a spectrometer) and an emitter 106 (e.g., a neutron source) mounted to the frame 102. The detector 104 may be mounted to the frame 102 with a detector bracket 114 and the emitter 106 may be mounted to the frame 102 with an emitter bracket 116. Each of the detector bracket 114 and the emitter bracket 116 may be sized and positioned on the frame 102 to orient the detector 104 and the emitter 106 substantially along one or more common planes.

In some embodiments, the detector 104 may comprise an ORTEC® trans-SPEC-100 high purity germanium (HPGe) spectrometer, available from AMETEK® Advanced Measurement Technology, Inc. of Oak Ridge, Tenn. Such a detector 104 may include a germanium crystal to detect radiation (e.g., gamma rays) emitted from an object being tested (e.g., munitions, any items suspected of containing chemical warfare agents, reactive materials, or explosive materials, etc.) and a signal processor (e.g., a digital signal processing multichannel analyzer (MCA)), for analyzing the detected radiation, and a mechanical cooling system (e.g., a Stirling cycle cooler). In other embodiments, the detector 104 may comprise a liquid nitrogen cooled HPGe detector.

The emitter 106 may comprise a neutron generator including a neutron tube module 108 and a control box 110. In some embodiments, the emitter 106 may comprise a deuterium-tritium (DT) neutron generator, a californium-252 neutron source, a deuteron-deuteron (DD) neutron generator, a deuteron-triton (DT) neutron generator, or combinations thereof. For example, the emitter 106 may comprise a THERMO SCIENTIFIC® P 385 or a THERMO SCIENTIFIC® MP 320, available from Thermo Fisher Scientific Inc. of Waltham, Mass. A mark 112 illustrates a plane in which the neutrons are generated in the emitter 106 emits neutrons along a target plane as discussed below.

The chemical detection system 100 includes one or more elements for separating (e.g., by at least partially isolating) the detector 104 from the emitter 106 (e.g., from the neutrons emitted from the emitter 106 at the slot 112) and from other background sources of radiation. For example, a shielding system 118 may be positioned between the detector 104 and the emitter 106. The shielding system 118 may include a first portion configured to protect the detector 104 from direct radiation emitted by the emitter 106 (e.g., one or more blocks 120 comprising a metal such as tungsten).

The shielding system 118 may include a second portion configured to direct the radiation emitted by the emitter 108 toward the object being tested (e.g., one or more moderator blocks 122 comprising a polymer material). For example, the moderator block 122 may comprises a thermoplastic such as high-density polyethylene (HDPE). The moderator block 122 may act to redirect at least some of the neutrons that are emitted from the slot 112 of the emitter 106 toward the object to be tested and may provide a flux of both fast neutrons and slow neutrons to the object to be tested. For example, the emitter 106 may emit fast neutrons in substantially all directions. Fast neutrons emitted away from the object to be tested may have their speeds reduced by the moderator block 122 changing them to slow or thermal neutrons and may be redirected by the moderator block 122 back toward the object to be tested. Fast neutrons emitted by the emitter 106 in a direction toward the object to be tested are not effected or are minimally effected by the moderator block 122 and remain fast neutrons. Fast and slow neutrons play complementary roles in the excitation of the fill chemical inside the object to be tested. For example, some chemical elements (e.g., phosphorus) are excited more efficiently by fast neutron inelastic scattering, while others (e.g., hydrogen and chlorine) are more efficiently excited by capture of slow neutrons. By disposing the moderator block 122 at least partially about the emitter 106 (e.g., at least partially surrounding) results in the redirection of neutrons that otherwise would be lost back toward the object to be tested.

Referring still to FIG. 2, the shielding system 118 of the chemical detection system 100 may include a collimator 124 positioned proximate the detector 104 to isolate the detector 104 from the radiation emitted by the emitter 106 and from other background sources of radiation by narrowing the beam of partials that are received by a nose portion 126 of the detector 104 that houses the germanium crystal. For example, as depicted in FIG. 2, the collimator 124 may substantially surround (e.g., entirely surround) the nose portion 126 of the detector 104.

Figure 3:
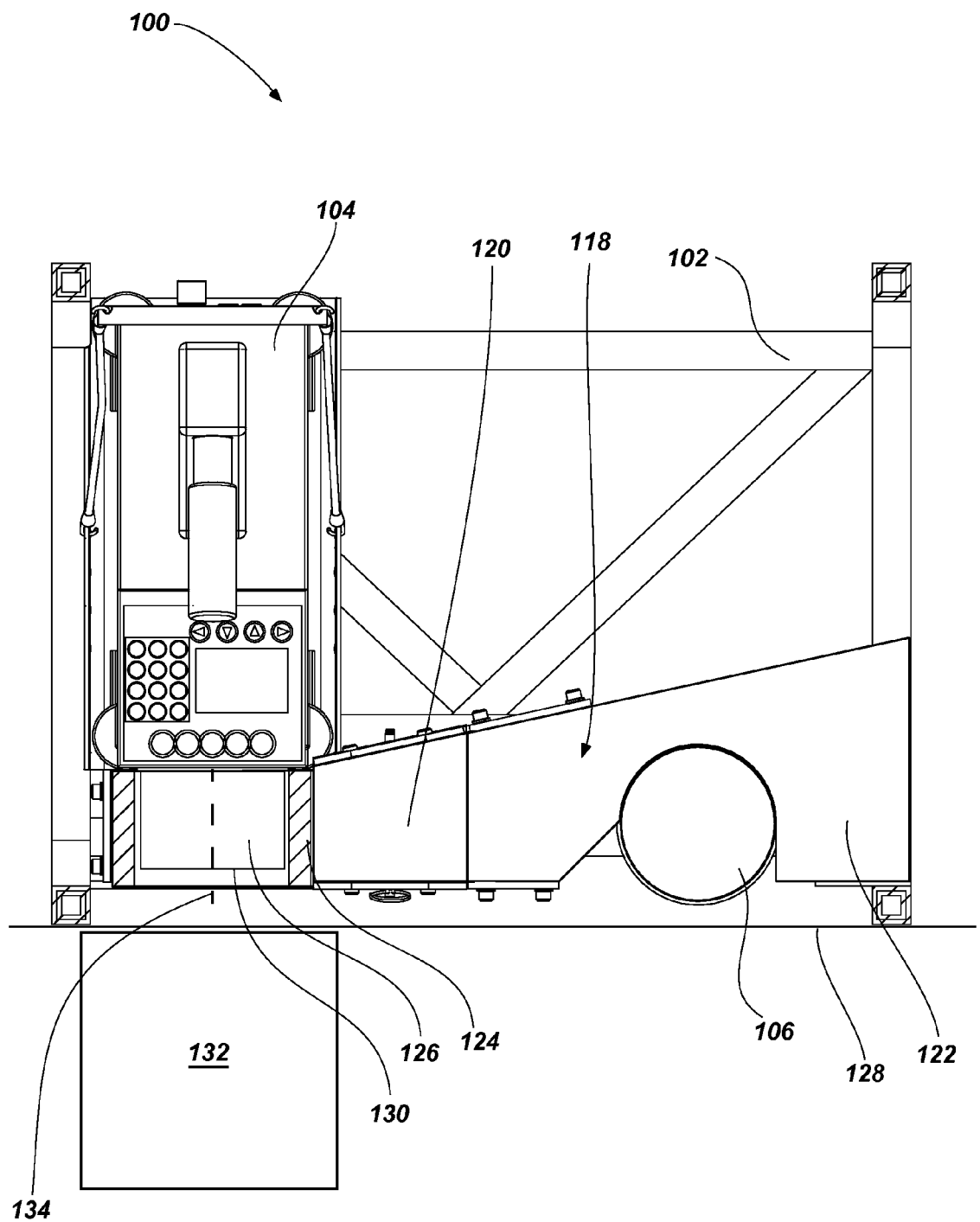
FIG. 3 is a top partial cross-sectional view of the chemical detection system shown in FIG. 2.

FIG. 3 is a top partial cross-sectional view of the chemical detection system 100 shown in FIG. 2. As shown in FIG. 3, the frame 102 of the chemical detection system 100 is configured to substantially orient the detector 104, the emitter 106, and shielding system 118 along (e.g., substantially parallel to, for example, ±15 degrees) a plane. For example, the frame 102 of the chemical detection system 100 is configured to substantially orient the detector 104, the emitter 106, and shielding system 118 along plane 128 shown extending along a front portion (e.g., a portion of the frame 102 at which radiation is detected by the detector 104) of the chemical detection system 100 (i.e., into the paper). For example, a sensing surface 130 of the nose portion 126 of the detector 104 (e.g., a surface of the nose portion 126 of the detector 104 that is exposed in the collimator 124 in order to enable transmission of radiation to the germanium crystal) may extend substantially parallel (e.g., directly parallel) to the plane 128 extending along the front portion of the frame 102. In some embodiments, an outermost portion of the collimator 124 that surrounds the nose portion 126 of the detector 104 may be oriented to extend substantially parallel (e.g., directly parallel) to the plane 128.

As depicted, an object to be tested 132 may be placed proximate the plane 128 and may be aligned with the detector 104. For example, the center of mass of the object to be tested 132 may be substantially aligned with the centerline 134 of the circular sensing surface 130 of the nose portion 126 of the detector 104 (e.g., along a central axis of the germanium crystal within the nose portion 126). In some embodiments, the object to be tested 132 may be centered in front of the transition between blocks 120 and a collimator 124. The orientation of the detector 104, emitter 106, and shielding system 118 may enable the object to be tested 132 to be placed proximate and extend along the chemical detection system 100. For example, orientation of the detector 104, emitter 106, and shielding system 118 along the plane 128 may provide robust scanning of the object to be tested 132 by enabling the chemical detection system 100 to be placed directly against the object to be tested 132 (e.g., a relatively large object such as a cargo container), enabling the chemical detection system 100 to be moved along the object to be tested 132, enabling the chemical detection system 100 to be placed over (e.g., on top of) the object to be tested 132, or combinations thereof.

Referring to both FIGS. 2 and 3, in some embodiments, the detector bracket 114 and the emitter bracket 116 may be sized and positioned on the frame 102 to orient the centerline 134 of the circular sensing surface 130 of the nose portion 126 of the detector 104 and the slot 112 of the emitter 106 to extend along a plane that extends along (e.g., contains) the centerline 134 of the detector 104. In other words, the detector bracket 114 and the emitter bracket 116 are sized and positioned on the frame 102 to position the centerline 134 of the detector 104 and the slot 112 of the emitter 106 at a similar distance from the base 103 of the frame 102.

Figure 4A:
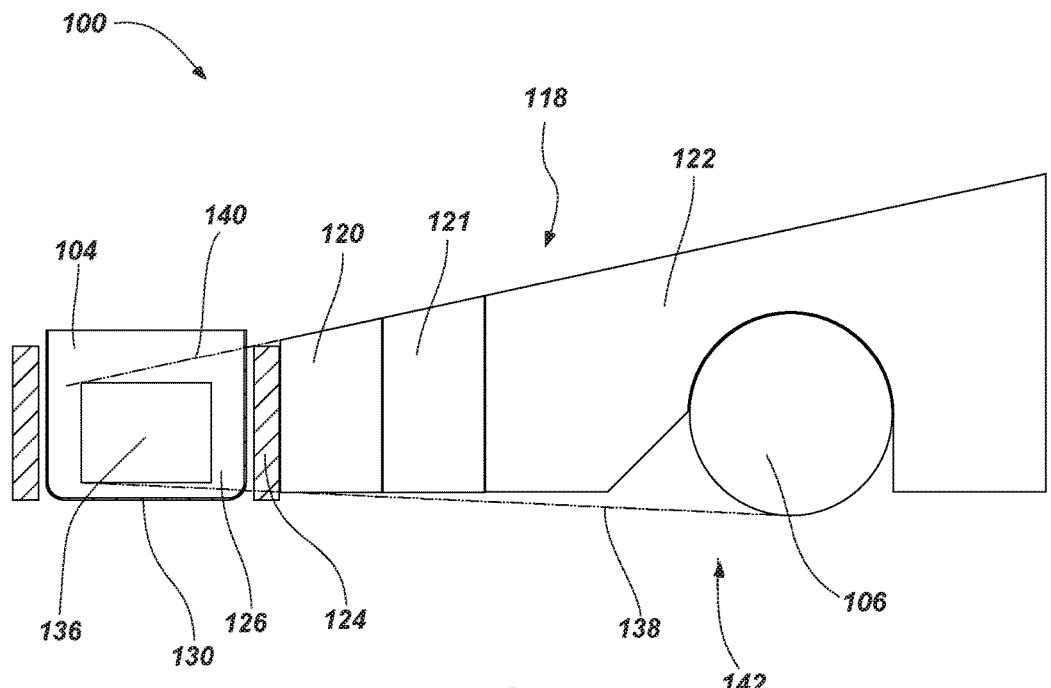
FIG. 4A is a top partial cross-sectional view of a portion of a chemical detection system such as the chemical detection system shown in FIGS. 2 and 3 in accordance with an embodiment of the present disclosure.

FIG. 4A is a top partial cross-sectional view of a portion of a chemical detection system such as the chemical detection system 100 shown in FIGS. 2 and 3. As shown in FIG. 4A, the detector 104 and the emitter 106 are separated by the shielding system 118 including two blocks 120, 121 (e.g., tungsten blocks), the moderator block 122, and the collimator 124 surrounding the nose portion 126 of the detector 104 that houses a crystal 136 (e.g., a germanium crystal). As depicted, the moderator block 122 at least partially surrounds the emitter 106 and includes opening 142 providing at least some of the neutrons generated by the emitter 106 (e.g., fast neutrons) a direct path of travel to the object to be tested 132 (FIG. 3). As shown by dashed line 138, the frame 102 (FIG. 2) of the chemical detection system 100 positions the detector 104 and the emitter 106 such that neutrons generated by the emitter 106 do not have a direct path to the crystal 136 within the detector 104. As shown by dashed line 140, the frame 102 (FIG. 2) of the chemical detection system 100 positions the detector 104 and the emitter 106 and the blocks 120, 121 are sized and oriented such that neutrons generated by the emitter 106 that may travel through the moderator block 122 do not have a direct path to the crystal 136 within the detector 104 as such neutrons would be blocked by one or more of the blocks 120, 121 and the collimator 124.

As discussed above, the blocks 120, 121, the moderator block 122, and the collimator 124 may act to isolate and/or redirect neutrons emitted from the emitter 106 and other background sources of radiation such that a majority of the radiation detected by the crystal 136 in the detector 104 will generally be directed from the object to be tested 132 (FIG. 3) and not from the emitter 106 and other background sources of radiation.

In some embodiments, the blocks 120, 121 and the moderator block 122 may have a thickness of about 3 inches (76.2 mm). For example, the blocks 120, 121 and the moderator block 122 may each be centered at the slot 112 (FIG. 2) of the emitter 106 and may extend 1.5 inches (38.1 mm) past the slot 112 in each direction along the length of the neutron tube module 108 (FIG. 2) of the emitter 106. In other words, the blocks 120, 121 and the moderator block 122 may extend 1.5 inches (38.1 mm) above and below the slot 112 in orientation of the emitter 106 as shown in FIG. 2. The combination of the blocks 120, 121 and the moderator 122 may separate the detector 104 from the emitter 106 by about 8 inches (203.2 mm). The portion of the moderator block 122 that at least partially surrounds the emitter 106 may have a minimum thickness of about 1.5 inches (38.1 mm). The collimator 124 may have a wall thickness of about 0.5 inch (12.7 mm).

Figure 4B:
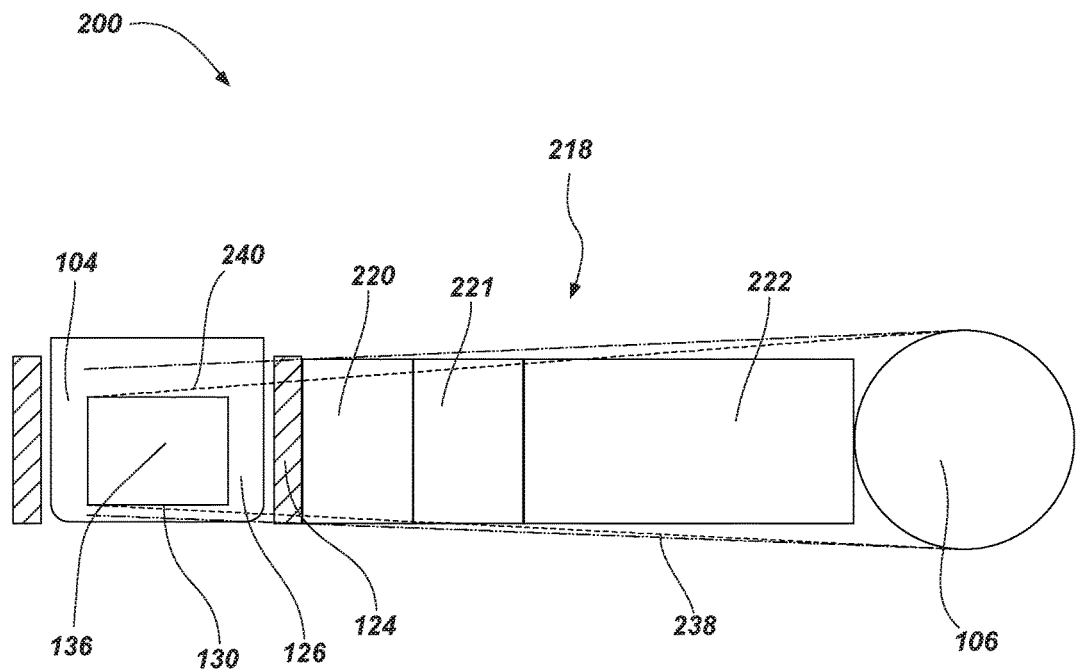
FIG. 4B is a top partial cross-sectional view of a portion of a chemical detection system in accordance with another embodiment of the present disclosure.

FIG. 4B is a top partial cross-sectional view of a portion of a chemical detection system 200 that may be somewhat similar to the chemical detection system 100 shown and described above with reference to FIGS. 1 through 3. As shown in FIG. 4B, the detector 104 and the emitter 106 are separated by a shielding system 218 including two blocks 220, 221 (e.g., tungsten blocks), the moderator block 222, and the collimator 124 surrounding the nose portion 126 of the detector 104 that houses the crystal 136. As depicted, a moderator block 122 may comprise a rectangular shape and may be positioned on one side of the emitter 106 (e.g., between blocks 220, 221 and the emitter 106). As shown by dashed lines 238, a frame (e.g., similar to frame 102 as shown in FIG. 2) of the chemical detection system 200 positions the detector 104 and the emitter 106 such that neutrons generated by the emitter 106 do not have a direct path to the crystal 136 within the detector 104 on a first side of the crystal 136. As shown by dashed lines 240, the frame of the chemical detection system 200 positions the detector 104 and the emitter 106 such that neutrons generated by the emitter 106 do not have a direct path to the crystal 136 within the detector 104 on a second side of the crystal 136. Further, neutrons generated by the emitter 106 that may travel through the moderator block 222 do not have a direct path to the crystal 136 within the detector 104 as such neutrons would be blocked by one or more of the blocks 120, 121 and the collimator 124.

As discussed above, the blocks 220, 221, the moderator block 222, and the collimator 124 act to one or more of isolate and redirect neutrons emitted from the emitter 106 and other background sources of radiation such that a majority of the radiation detected by the crystal 136 in the detector 104 will generally be directed from the object to be tested 132 (FIG. 3) and not from the emitter 106 and other background sources of radiation.

Similar to the shielding system 118 above, in some embodiments, the blocks 220, 221 and the moderator block 222 may have a thickness of about 3 inches (76.2 mm). For example, the blocks 220, 221 and the moderator block 222 may each be centered at the slot 112 (FIG. 2) of the emitter 106 and may extend 1.5 inches (38.1 mm) past the slot 112 in each direction along the length of the neutron tube module 108 (FIG. 2) of the emitter 106. In other words, the blocks 220, 221 and the moderator block 222 may extend 1.5 inches (38.1 mm) above and below the slot 112 in orientation of the emitter 106 as shown in FIG. 2. The combination of the blocks 220, 221 and the moderator block 222 may separate the detector 104 from the emitter 106 by about 10 inches (254 mm).

Figure 5:
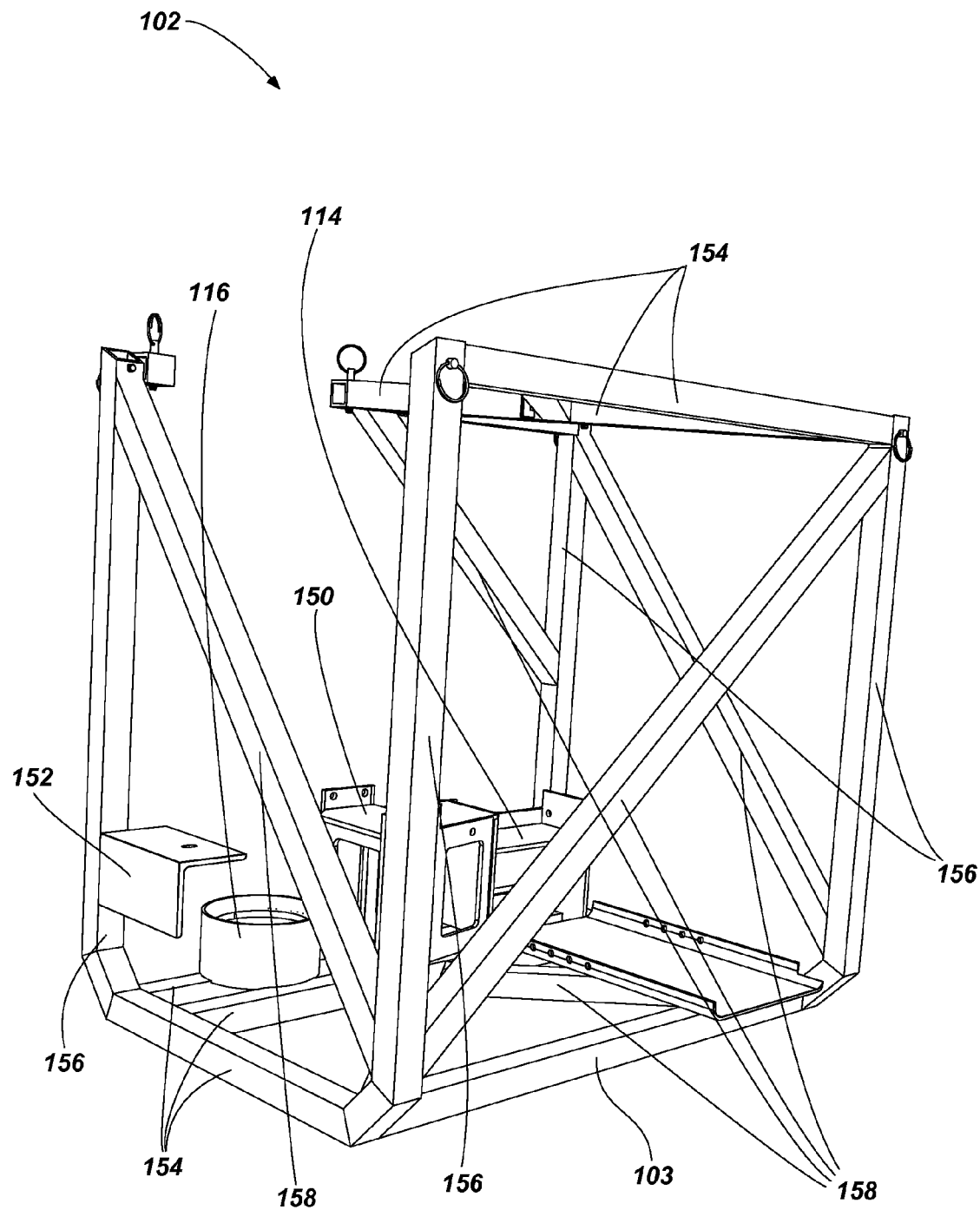
FIG. 5 is a perspective view of a frame for a chemical detection system such as the frame of the chemical detection system shown in FIGS. 2 and 3 in accordance with an embodiment of the present disclosure.

FIG. 5 is a perspective view of a frame for a chemical detection system such as the frame 102 of the chemical detection system 100 shown in FIGS. 2 and 3. As shown in FIG. 5, the frame 102 includes the detector bracket 114 and the emitter bracket 116 that are coupled to the frame 102. As depicted, the detector bracket 114 may include a portion 150 for mounting a portion of the shielding system 118 (FIG. 2) (e.g., block 120 and a side of the moderator block 122 (FIG. 2)). The frame 102 may include another bracket 152 for mounting another portion of the shielding system 118 (FIG. 2) (e.g., another side of the moderator block 122 (FIG. 2)). The frame 102 may include a plurality of lateral members 154, longitudinal members 156, and one or more crossbars 158 that are coupled together (e.g., via weld, pins, etc.). As discussed above, and also referring to FIG. 2, each of the detector bracket 114 and the emitter bracket 116 may be sized and positioned on the frame 102 to orient the detector 104 and the emitter 106 substantially along one or more common planes. The frame 102 (e.g., the detector bracket 114, the emitter bracket 116, and bracket 152) may be sized and configured to position the shielding system 118 relative to the detector 104 and the emitter 106. For example, as discussed above, each of the shielding system 118, the detector 104, and the emitter 106 may extend substantially along a common plane.

In some embodiments, the frame 102 may a provide a chemical detection system that is at least partially self-contained (e.g., portable) that may be positioned next to objects or moved along objects to be tested that are not readily movable (e.g., objects at least partially within the ground, large objects such as cargo containers, etc.).

Figure 6A:
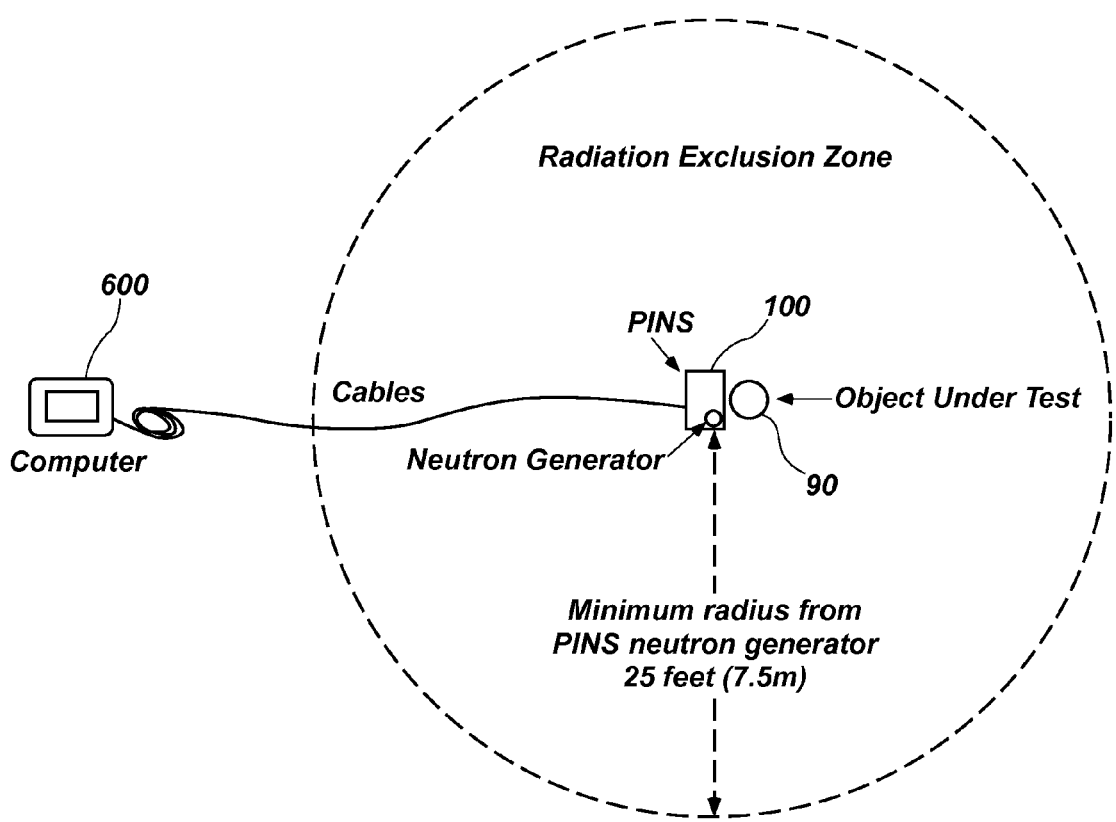
FIG. 6A illustrates an example placement of the chemical detection system relative to an object under test and a computing system.

FIG. 6A illustrates an example placement of the chemical detection system 100 relative to an object under test 90 and a computing system 600. Because there is danger of radiation exposure from the neutron generator, an "Exclusion Zone" surrounding the point where the chemical detection system 100 will be used. No one should be allowed inside this zone while the generator is producing neutrons. An example radiation exclusion zone is shown in FIG. 6A. The computing system 600 can be placed outside the exclusion zone and connected to the spectrometer electronics via a suitable communication cable, such as, for example, a serial cable, a parallel cable, an Ethernet cable, and a USB cable. Alternatively, the computing system and the spectrometer electronics can communicate with wireless protocols it they are so equipped.

Figure 6B:
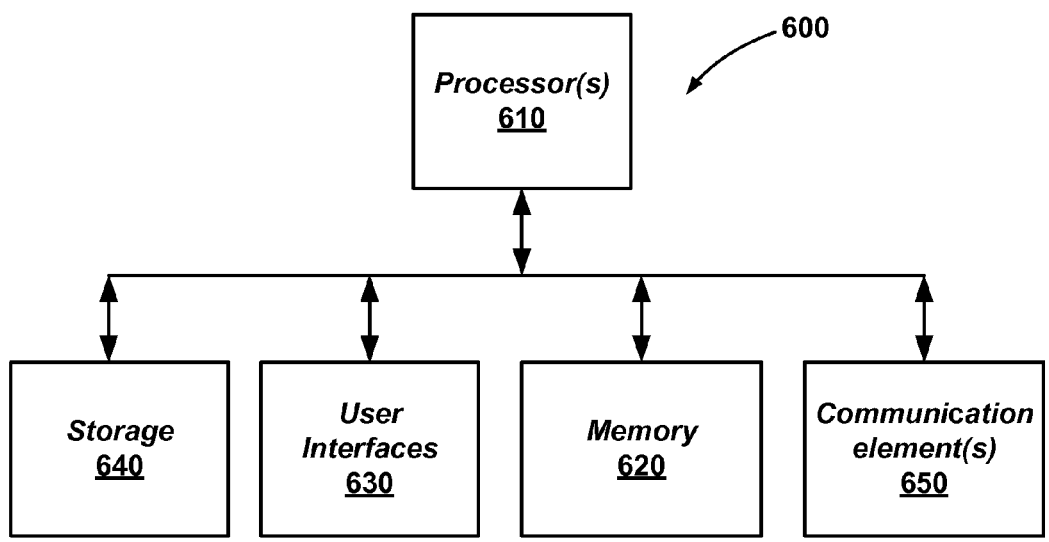
FIG. 6B illustrates a computing system for practicing some embodiments of the present disclosure.

FIG. 6B illustrates a computing system 600 for practicing embodiments of the present disclosure. Computer, computing system, and server may be used interchangeably herein to indicate a system for practicing some embodiments of the present disclosure. The computing system 600 is configured for executing software programs containing computing instructions and includes one or more processors 610, memory 620, one or more communication elements 650, user interface elements 630, and storage 640.

As non-limiting examples, the computing system 600 may be a user-type computer, a file server, a compute server, a notebook computer, a tablet, a handheld device, a mobile device, or other similar computer system for executing software.

The one or more processors 610 may be configured for executing a wide variety of operating systems and applications including the computing instructions for carrying out embodiments of the present disclosure.

The memory 620 may be used to hold computing instructions, data, and other information for performing a wide variety of tasks including performing embodiments of the present disclosure. By way of example, and not limitation, the memory 620 may include Synchronous Random Access Memory (SRAM), Dynamic RAM (DRAM), Read-Only Memory (ROM), Flash memory, and the like.

Information related to the computing system 600 may be presented to, and received from, a user with one or more user interface elements. As non-limiting examples, the user interface elements 630 may include elements such as displays, keyboards, mice, joysticks, haptic devices, microphones, speakers, cameras, and touchscreens. A display on the computing system 600 may be configured to present a graphical user interface (GUI) with information about some embodiments of the present disclosure, as is explained below.

The communication elements 650 may be configured for communicating with other devices or communication networks. As non-limiting examples, the communication elements 650 may include elements for communicating on wired and wireless communication media, such as, for example, serial ports, parallel ports, Ethernet connections, Universal Serial Bus (USB) connections IEEE 1394 ("firewire") connections, BLUETOOTH® wireless connections, 802.1 a/b/g/n type wireless connections, and other suitable communication interfaces and protocols.

The storage 640 may be used for storing relatively large amounts of non-volatile information for use in the computing system 600 and may be configured as one or more storage devices. By way of example, and not limitation, these storage devices may include computer-readable media (CRM). This CRM may include, but is not limited to, magnetic and optical storage devices such as disk drives, magnetic tapes, CDs (compact discs), DVDs (digital versatile discs or digital video discs), and other equivalent storage devices.

Software processes illustrated herein are intended to illustrate representative processes that may be performed by the systems illustrated herein. Unless specified otherwise, the order in which the process acts are described is not intended to be construed as a limitation, and acts described as occurring sequentially may occur in a different sequence, or in one or more parallel process streams. It will be appreciated by those of ordinary skill in the art that many steps and processes may occur in addition to those outlined in flowcharts. Furthermore, the processes may be implemented in any suitable hardware, software, firmware, or combinations thereof.

When executed as firmware or software, the instructions for performing the processes may be stored on a computer-readable medium. A computer-readable medium includes, but is not limited to, magnetic and optical storage devices such as disk drives, magnetic tape, CDs (compact disks), discs), DVDs (digital versatile discs or digital video discs), and semiconductor devices such as RAM, DRAM, ROM, EPROM, and Flash memory.

By way of non-limiting example, computing instructions for performing the processes may be stored on the storage 640, transferred to the memory 620 for execution, and executed by the processors 610. The processors 610, when executing computing instructions configured for performing the processes, constitutes structure for performing the processes and can be considered a special-purpose computer when so configured. In addition, some or all portions of the processes may be performed by hardware specifically configured for carrying out the processes.

Elements are the basic building blocks of chemistry. Combinations of elements are referred to as compounds. The PINS software does not detect compounds; rather it detects the elements that combine into compounds. By identifying these elements and their amounts in relation to one another, PINS can infer the identity of various compounds. PINS identification of explosive compounds and mixtures may employ a decision tree type of logic shown and discussed below with reference to FIG. 10. PINS uses multiplicative factors to determine confidence levels for all the potential fills.

The PINS apparatus uses neutrons produced by an electrical neutron generator to excite nuclei inside the object under test. Inside the generator, the heavy isotopes of hydrogen, deuterium ($^2$D) and tritium ($^3$T), collide and form an alpha particle ($^4$He) plus a neutron (n) in a nuclear fusion reaction, which can be expressed as:

$$^2D + {}^3T \rightarrow {}^4He + n.$$

Alternatively, the electrical neutron generator may employ the deuterium (2D)-deuterium (2D) nuclear fusion reaction, producing a 3He nucleus and a neutron (n), and this reaction may be expressed as:

$$2D + 2D \rightarrow {}^3He + n.$$

Nuclear fusion reactions are exothermic, and the deuterium-deuterium (DD) reaction produces 2.5 Megaelectron Volt (MeV) neutrons, and the deuterium-tritium (DT) reaction produces 14.1 Megaelectron Volt (MeV) neutrons. The neutron generator may produce about ten million neutrons per second.

Neutrons from the neutron generator excite the nuclei they encounter chiefly by inelastic scattering or, less frequently, by neutron capture. In either case, the excited nuclei decay to their ground states by gamma-ray emission, and the gamma-rays are characteristic of the emitting nucleus. That is, the gamma-ray energies and intensities vary, often strongly, from one nucleus to another. For example, the carbon nucleus emits about a 4.4-MeV gamma ray under neutron bombardment, while an oxygen nucleus emits about a 6.1-MeV gamma-ray.

The neutron-induced gamma rays are measured by a spectrometer (e.g., a high-purity germanium (HPGe) spectrometer) and may be sorted into a spectrum by associated spectrometer electronics. By analysis of the spectrum, the chemical elements excited by the neutrons can be identified, and the chemical inside the object under test can be identified.

Unlike the HPGe spectrometers used in previous PINS systems, embodiments of the present disclosure uses a mechanically-cooled HPGe detector, requiring electricity but no liquid nitrogen for cooling. The electrical power required is about 30 watts, and the system's lithium ion batteries can keep the detector cold for about 10 to 12 hours.

Spectroscopy is the art of measuring and interpreting wavelength-intensity (may also be referred to as "energy-intensity patterns" or "spectra.") Gamma-ray spectra are graphs of gamma-ray intensity versus gamma-ray energy. Each gamma-ray spectrum for embodiments of the present invention may include over 100 vertical spikes (i.e., "peaks") and these peaks may be used as keys to interpretation of the gamma-ray spectrum.

Figure 7:
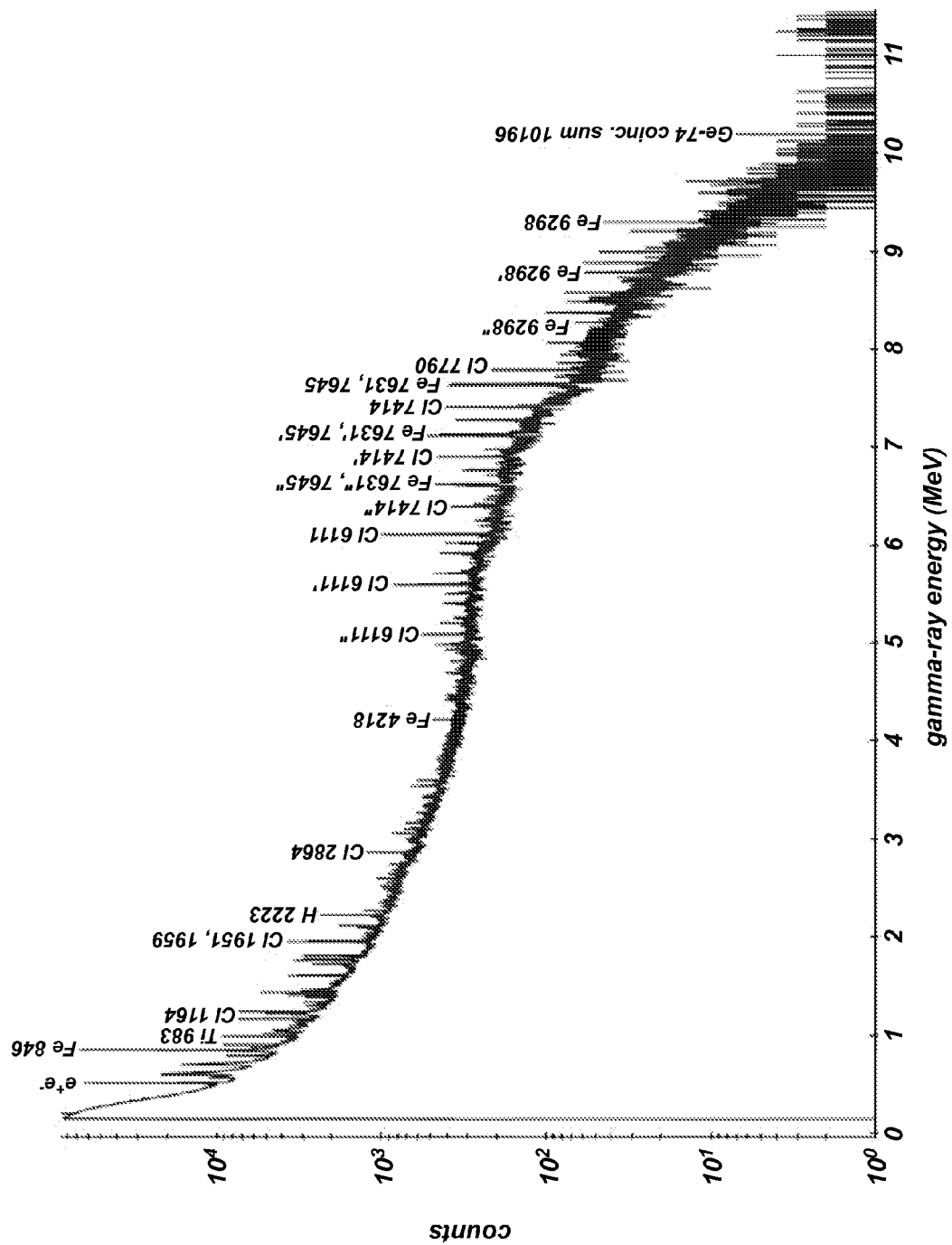
FIG. 7 illustrates an example of a gamma-ray spectrum.

FIG. 7 illustrates an example of a gamma-ray spectrum. Many of the gamma-ray peaks carry redundant information, and embodiments of the present disclosure can sometimes generate result by analysis of five peaks or less.

Some of the stronger peaks in FIG. 7 have been labeled with the emitting chemical element symbol and the gamma-ray peak energy. For example, the peak labeled "Cl 6111" was emitted by a chlorine (Cl) nucleus, and its gamma-ray energy is 6111 keV. In general, gamma-ray spectra may be too complex to analyze by a user viewing the spectra without zooming into a selected spectral region or regions to see the details as discussed below with reference to FIGS. 9A and 9B.

Figure 8:
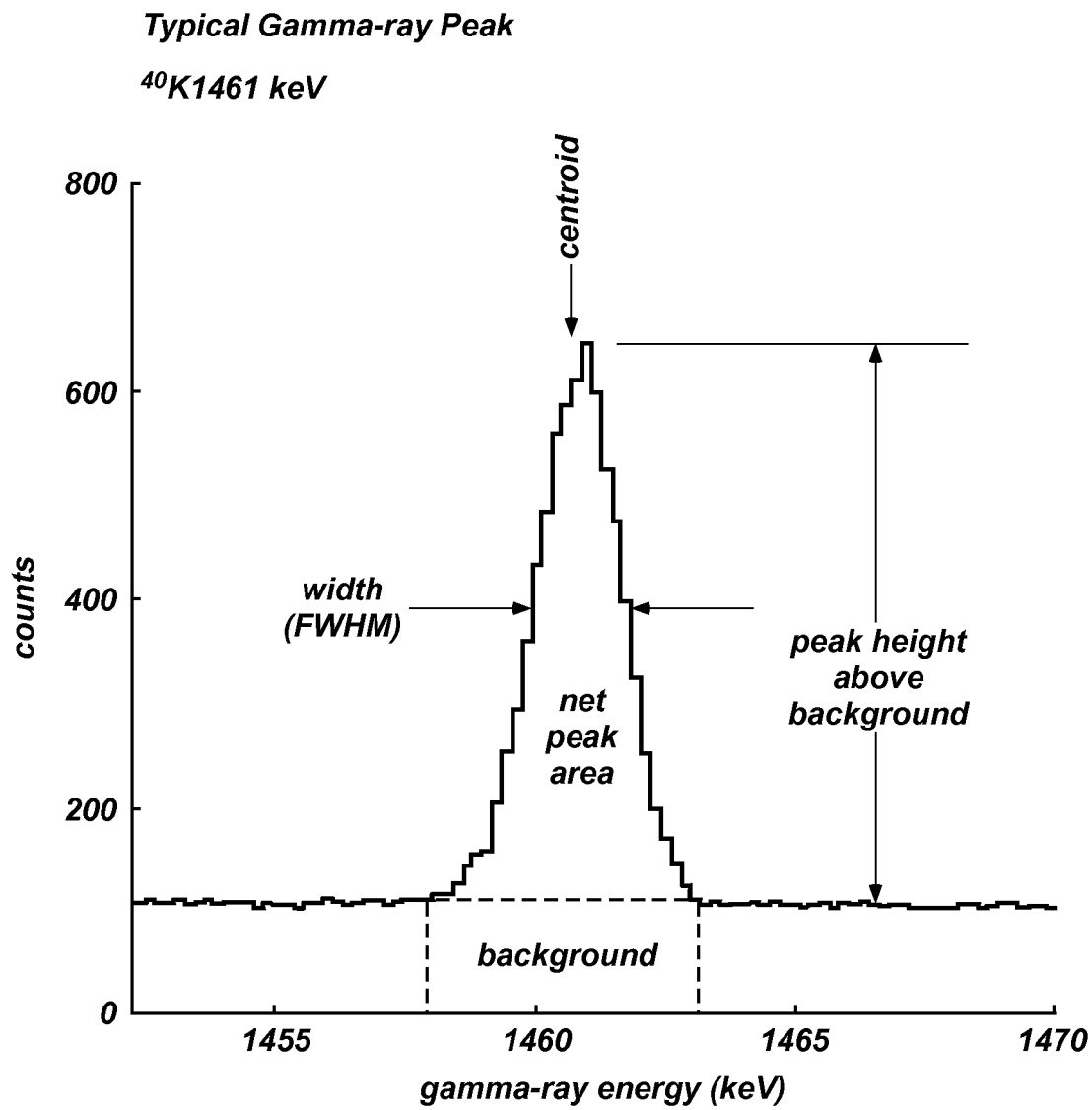
FIG. 8 illustrates some details of a gamma-ray peak.

FIG. 8 illustrates some details of a gamma-ray-peak 810. Some embodiments may analyze gamma-ray peaks individually or in small groups A gamma ray gamma-ray peak may have several notable attributes. The most obvious feature is the peak height, or, when a peak sits upon a continuous background, as in FIG. 8, the peak's height above background. The centroid, which is the midpoint of the peak's count distribution, denotes the energy of the gamma-ray peak, and the energy of a gamma-ray peak may be used to identify the emitting chemical element. As a result, determination of gamma-ray peak energies is useful for correct interpretation of spectra. As discussed herein, gamma-ray energies are stated in kiloelectron volts (keV) or megaelectron volts (MeV).

Other peak attributes include its height, width, and area. Gross or total peak area may be obtained by simply summing the number of counts from the lower-energy edge of a peak to the upper energy edge. A net peak area may be defined as the gross peak area, less the background area under the peak. In some embodiments, the net peak areas are directly proportional to the mass of a given chemical element within the test object. Along with peak energies, net peak areas and their related uncertainties are useful information extracted from a spectrum.

Most gamma-ray peaks sit on a jagged background called the Compton continuum. The background area under a peak can be subtracted from the gross peak area to determine the net peak area. Alternatively, using computer-based analytical techniques, a Gaussian curve can be fit to the peak atop a line segment that reflects the average Compton background.

By summing the area under the peak, and above the background, embodiments of the present disclosure can determine the net peak area in counts. The intensity of the gamma-ray peak is directly related to the net peak area. In addition, the intensity of a gamma-ray peak is proportional to a chemical element's concentration inside the munition, container, or other item under test that is being assessed.

By eye, the peak in FIG. 8 appears be a real peak, but what is the confidence that it is a real peak? If the net peak area is considered to be 826.9 counts plus or minus 45.1 counts, then one can define an uncertainty ratio, $t2=(826.9/45.1)=18.3$. As an approximation, peaks with a t2 ratio of 3 or greater may have a high statistical confidence level, and peaks with a t2 value exceeding 5 are very likely to be true peaks. Candidate peaks with t2 values less than 1 are likely fluctuations in the Compton background.

Computer analysis of gamma-ray peaks, either by summing or peak-fitting methods, determines the net peak areas and peak centroid energies with good precision. A curve-fitting method is especially useful in the analysis of complex gamma-ray spectra like those produced by embodiments of the present disclosure. This is fortunate, because hand-analysis of over 100 peaks in a typical gamma-ray spectrum would be quite tedious, especially since the computer may be configured to re-analyze a spectrum periodically (e.g., every 2-10 seconds) during data acquisition.

Embodiments of the present disclosure include three principal components: a neutron generator, a gamma-ray spectrometer, and control computer. Some embodiments may use an electrical neutron generator instead of the californium-252 neutron source used in earlier PINS instruments. The neutron generator accelerates deuterium (2H) ions into a tritium (3H) target, producing 14-MeV neutrons via the deuterium-tritium (DT) fusion reaction.

The gamma-ray spectrometer used with some embodiments may be mechanically-cooled, rather than liquid-nitrogen-cooled. The spectrometer may include a high-purity germanium (HPGe) detector, a digital signal processing multichannel analyzer (MCA), an internal battery, and an electrical-powered Stirling-cycle refrigerator. The spectrometer communicates with the computer with any suitable communications means as discussed above.

The computing system may be configured to serve as a control panel for controlling the interrogation process and provide the user with dynamic information regarding the progress of the interrogation process. As a non-limiting example, the computer may be configured to allow the user to start and stop the neutron generator, start and stop data acquisition by the gamma-ray spectrometer, and display and analyze the resulting gamma-ray spectra in substantially real time during the data acquisition. In wired configurations, connecting cables (e.g., 30 meters long) allow the computing system to be set up well outside the radiation exclusion area, and the cables provide communication between the control computer and the neutron generator and gamma-ray spectrometer.

Many gamma-ray spectrometers require temperatures near the boiling point of liquid nitrogen (i.e., −196° C. or −320° F.) to function correctly. Unlike other PINS HPGe detectors, embodiment of the present disclosure are cooled by an electrical-powered Stirling-cycle refrigerator, not by liquid nitrogen. Cooling the detector from room temperature typically requires 12 hours. Once cold, the detector may remain cold as long as its refrigerator keeps operating.

An indicator of spectrum quality is energy resolution. In other words, the system's ability to distinguish between two gamma-ray peaks closely spaced in energy may assist in defining various elements. Ideally, a gamma-ray spectrum reveals distinct peaks, with obvious valleys between them that extend nearly to the baseline of the overall spectrum. In contrast, poor resolution appears "fuzzy," with shorter peaks and filled-in valleys.

Figure 9B:
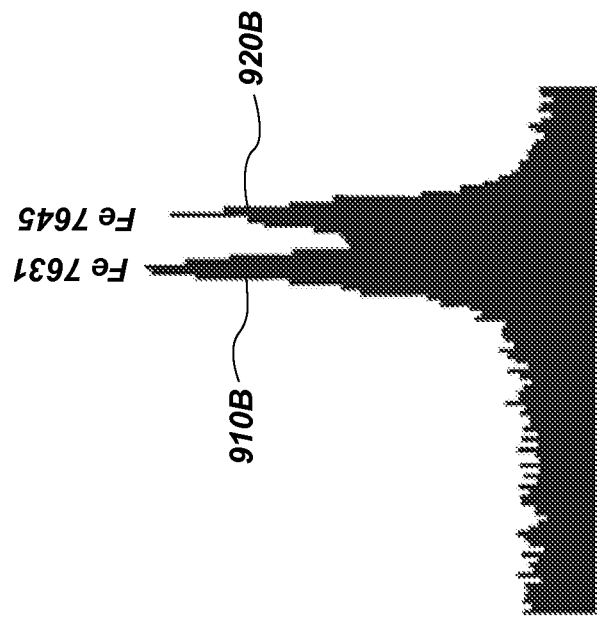
FIGS. 9A and 9B illustrate a zoomed-in view of iron peaks in a gamma-ray spectra exhibiting good and bad energy resolution.
Figure 9A:
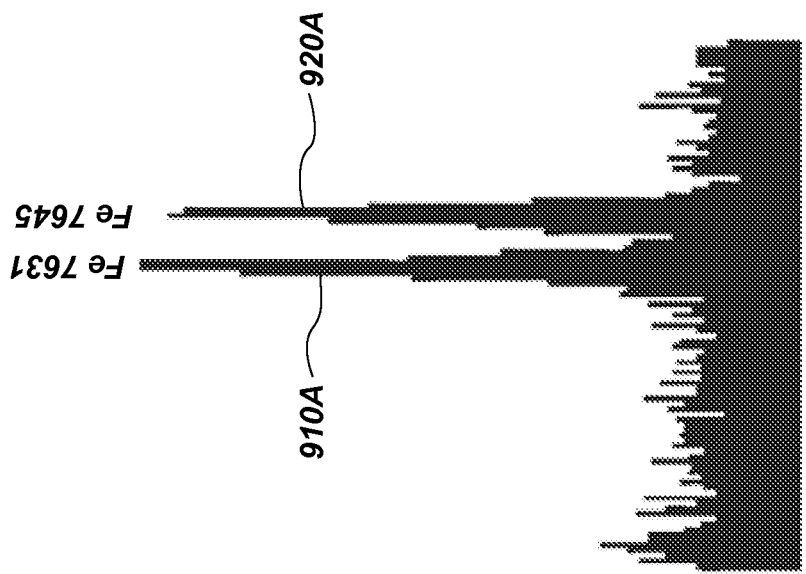

FIGS. 9A and 9B illustrate a gamma-ray spectrum a typical iron doublet used to check spectrometer energy resolution. Both of FIGS. 9A and 9B are from an assay of the same object; however, in FIG. 9B, a gain shift may have occurred during data acquisition. As a result, peaks 910B and 920B have a relatively poor resolution index of about 52%, whereas peaks 910A and 920A in FIG. 9A have a relatively good resolution index of about 96%. Good resolution tells the operator that data are being consistently sorted into precise channels. Poor resolution indicates that data are not being sorted as precisely, or that not enough data are available. A warm or damaged detector, a sudden gain shift, incorrect high voltage, high dead times, an electrical ground loop, or moisture on the detector all can cause poor energy resolution.

Figure 10:
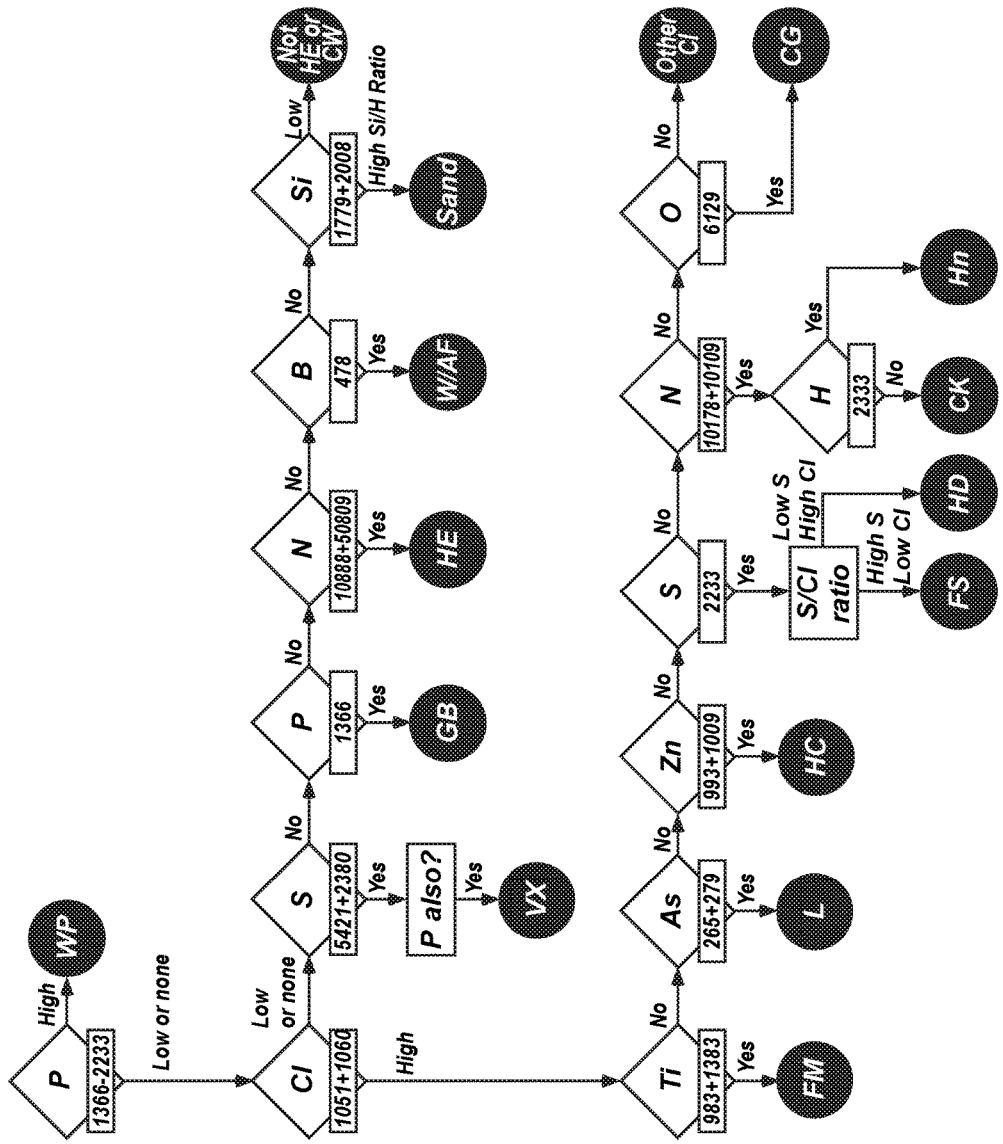
FIG. 10 illustrates a simplified decision tree illustrating decisions that may be made in an embodiment for detecting chemical weapons.

FIG. 10 illustrates a simplified decision tree illustrating decisions that may be made in an embodiment for detecting chemical weapons. Assume that two titanium gamma-ray peaks are evident (e.g., at 983 and 1381 keV) and two chlorine peaks appear (e.g., at 1165 and 1220 keV). No other chemical elements, including arsenic, boron, hydrogen, nitrogen, phosphorus, silicon, sulfur, or zinc, were detected in this spectrum.

Tracing through the decision tree shown in FIG. 10, one can start at the upper left and at each branch point, move down or to the right, depending on detection or non-detection of the branch-point chemical element. At the upper left of the decision tree, the first branch point is for the element phosphorus (P). Phosphorus was not detected in our assumption, and one moves down to the chlorine (Cl) branch point. Chlorine was detected in our assumption, and next one moves down to the titanium (Ti) branch point. Titanium was detected in our assumption, and hence the fill chemical may be FM smoke, also known as titanium tetrachloride.

Different paths through the decision tree lead to different fill chemical determinations. Note that the chlorine branch point roughly divides the possible fill chemicals in half: the upper row of chemicals, including the nerve agents and explosives, contain little or no chlorine. Nerve agent GB often contains a small amount of chlorine as an impurity. The lower row of chemicals, including mustard agent, lewisite, phosgene, and three types of smoke chemicals, all contain chlorine.

Figure 11:
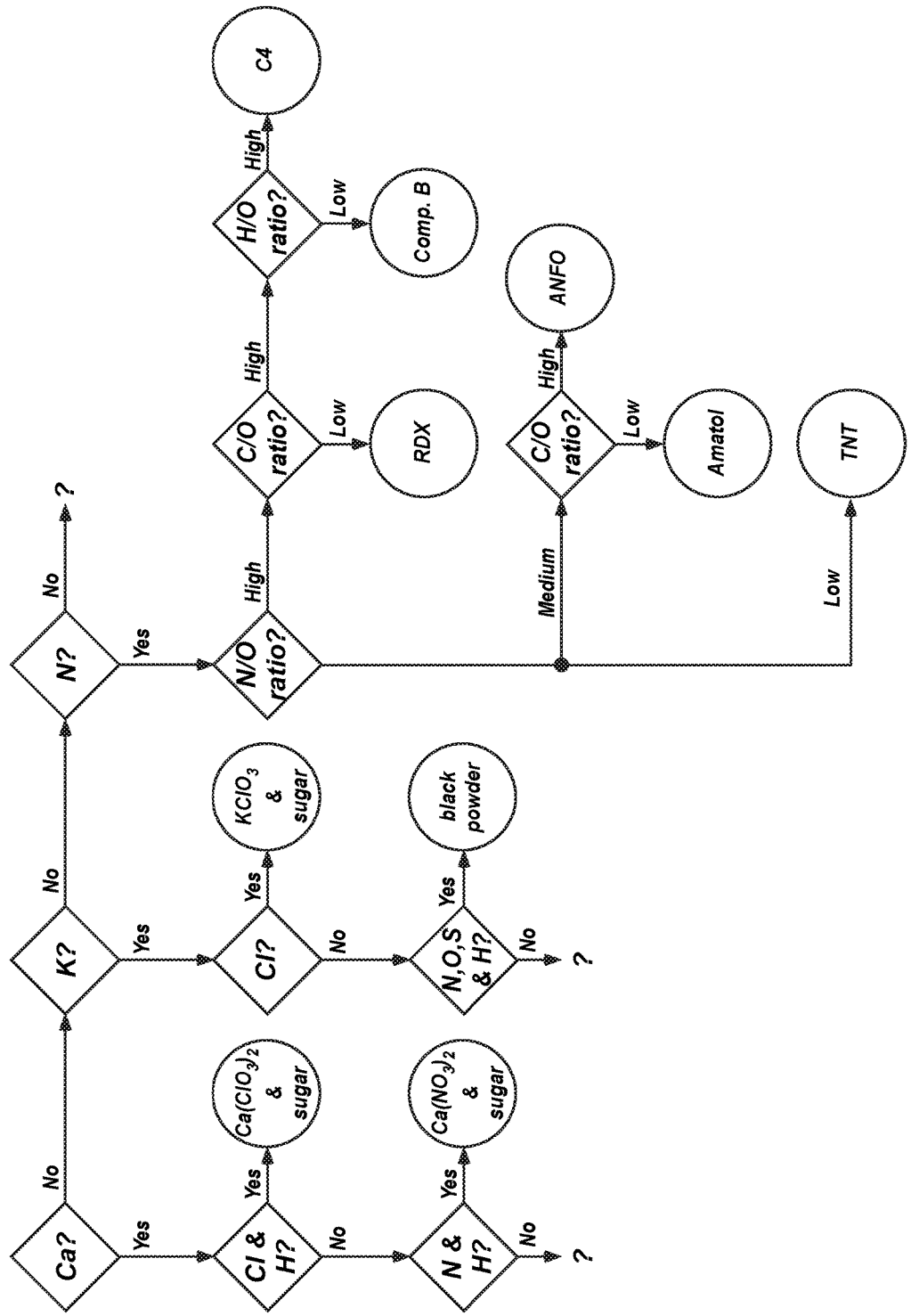
FIG. 11 illustrates a simplified decision tree illustrating decisions that may be made in an embodiment for detecting explosives.

FIG. 11 illustrates a simplified decision tree illustrating decisions that may be made in an embodiment for detecting explosives. As with FIG. 10, one can start at the upper left and at each branch point, move down or to the right, depending on detection or non-detection of the branch-point chemical element.

As an example of following the decision tree, assume that peaks are present that identify the presence of nitrogen (N), and oxygen (O). At the upper left of the decision tree, the first branch point is for the element calcium. Calcium is not presently identified so the decision tree progresses to the right for the element potassium. Potassium is not presently identified so the decision tree progresses to the right for the element nitrogen. Nitrogen is presently identified so the decision tree progresses down a decision about the ratio of nitrogen to oxygen. Assuming a low ratio, the decision tree indicates that the explosive may be TNT.

The decision trees of FIGS. 10 and 11 are simplified in that they don't indicate confidence levels for presence of each of the elements. Embodiments of the present invention may provide substantially real-time indications for confidence levels for given elements and compounds. Moreover, as a test progresses, these confidence levels may change. Therefore, this decision tree may be performed many times during a test to indicate confidence levels for various compounds during the test. As such, multiple branches of the decision tree may be processed, such that a confidence level is indicated for many of the compounds being evaluated.

PINS identification of the fill chemical relies on the presence and absence of elemental spectral lines in the neutron-induced gamma-ray spectrum and the related spectral line intensity ratios.

Until recently, chemical fill identification was determined with a decision tree, implemented in software by complex set of nested IF and ELSE statements. A disadvantage of the decision tree was that unless the unknown fill very closely resembled a candidate fill, no match would be made. The decision in this case would be made by the PINS scientists after the data were gather based on visual inspection of the spectrum. The new approach presented here is thus motivated by the desire to include this "expert knowledge." In effect, every path down the decision tree is now evaluated, and every node of the tree is a probabilistic function of a characteristic spectral signature. In embodiments of the present disclosure, the PINS software includes the decision algorithm comprised of a set of algebraic equations, one for each candidate fill. Each equation is a product of functions, where each function incorporates a signature characteristic of that candidate fill type.

As a result of this new decision algorithm, fill identification includes: (1) all candidate fills are independently matched to the unknown fill, so allowing multiple identification possibilities; (2) expert knowledge is easily incorporated into the candidate fill equations; (3) additional candidate fills are easily added to the algorithm; and (4) fill identifications can often be made early in an interrogation, as candidate fills are eliminated by the algorithm as the interrogation proceeds.

Figure 12C:
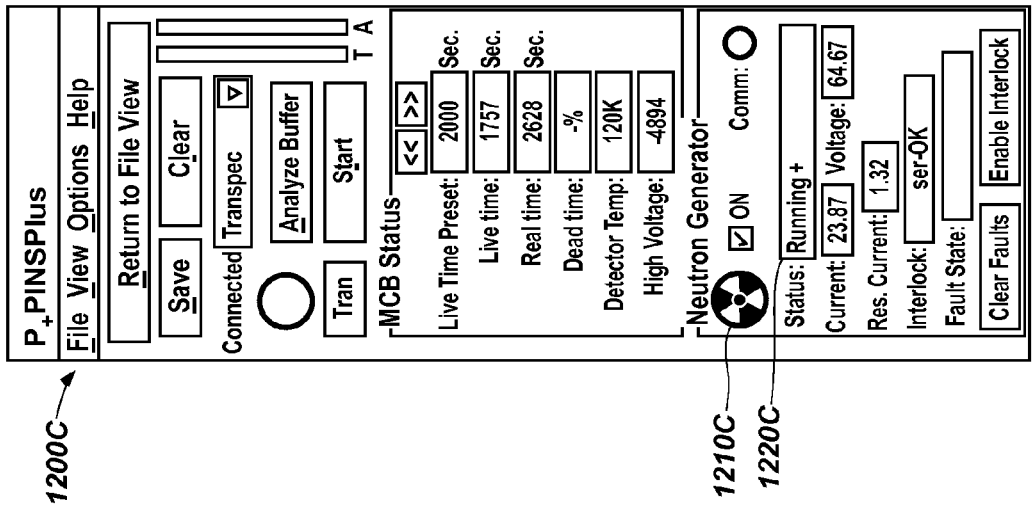
FIGS. 12A-12C illustrate a portion of a GUI that may be displayed to show status and control for the neutron generator and gamma-ray spectrometer.
Figure 12B:
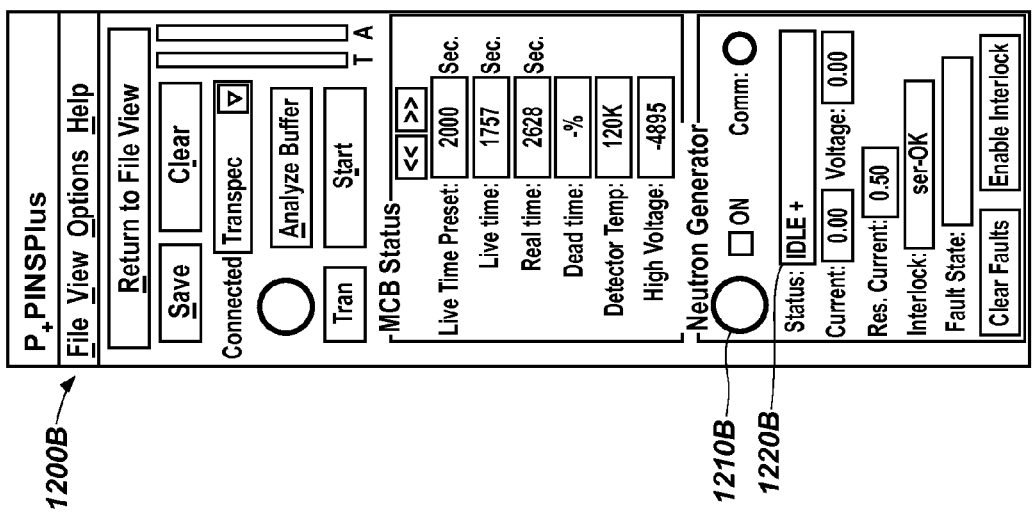
Figure 12A:
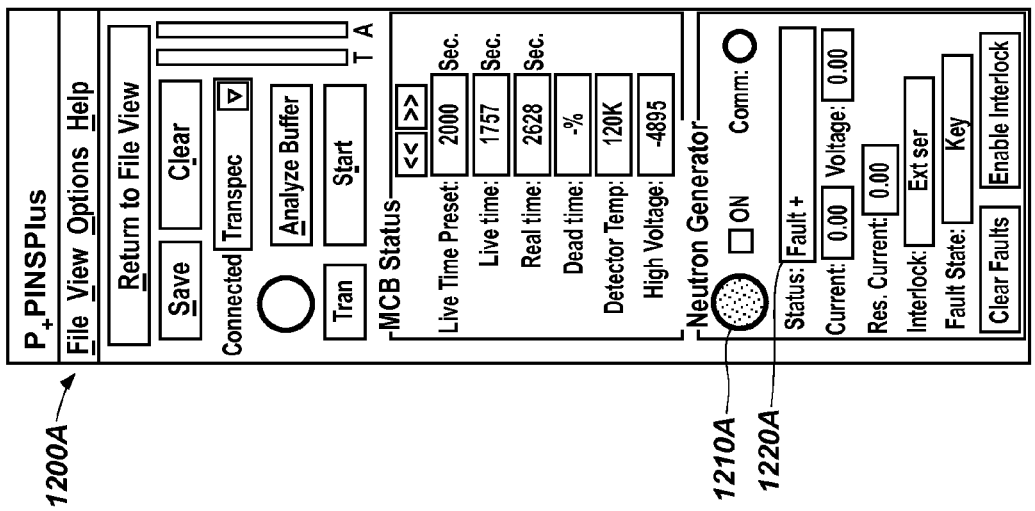

FIG. 12A-12C illustrate a portion of a GUI (1200A, 1200B, 1200C) that may be displayed to show status and control for the neutron generator and gamma-ray spectrometer. A region near the center of the displays labeled "MCB status" illustrates status of the spectrometer electronics, where MCB represents Multi-Channel Buffer. In this embodiment the center portion gives information about live time, real time, dead time, dead time percentage, detector temperature and detector voltage.

The computing system may compute the elapsed time of an assay in two ways. Real time is simply the elapsed time as measured by a stopwatch or a clock. Live time is the elapsed time, corrected for the time lost by the system electronics processing each gamma-ray event. At very low count rates, the real time and live time are nearly equal. At the higher count rates used in some embodiments, real time and live time may be significantly different, and this difference is usually expressed as a fractional dead time, calculated with the ratio:

dead time=(real time−live time)/real time

Dead times above 40 percent may cause poor energy resolution due to pulse pile-up effects.

The lower region of the displays labeled "Neutron Generator" give status and control information for the neutron generator. A first indicator 1210A, 1210B, and 1210C may be configured to give a quick easy indicator of status. A second indicator 1220A, 1220B, 1220C may give additional information about the status. As a non-limiting example, in FIG. 12A, the second status indicator 1220A indicates a fault and the first status indicator 1210A shows as red to indicate that the neutron generator is not working properly. Following the same example, if the fault is fixed, in FIG. 12B, the second status indicator 1220B indicates an idle condition and the first status indicator 1210B shows as yellow to indicate that the neutron generator is ready to operate. In this state, the operator can check the box labeled "ON" next to the first status indicator 1210B to start the neutron generator. Finally, in FIG. 12C, the second status indicator 1220C indicates a running condition and the first status indicator 1210C shows as a symbol to indicate that the neutron generator is running.

Figure 13:
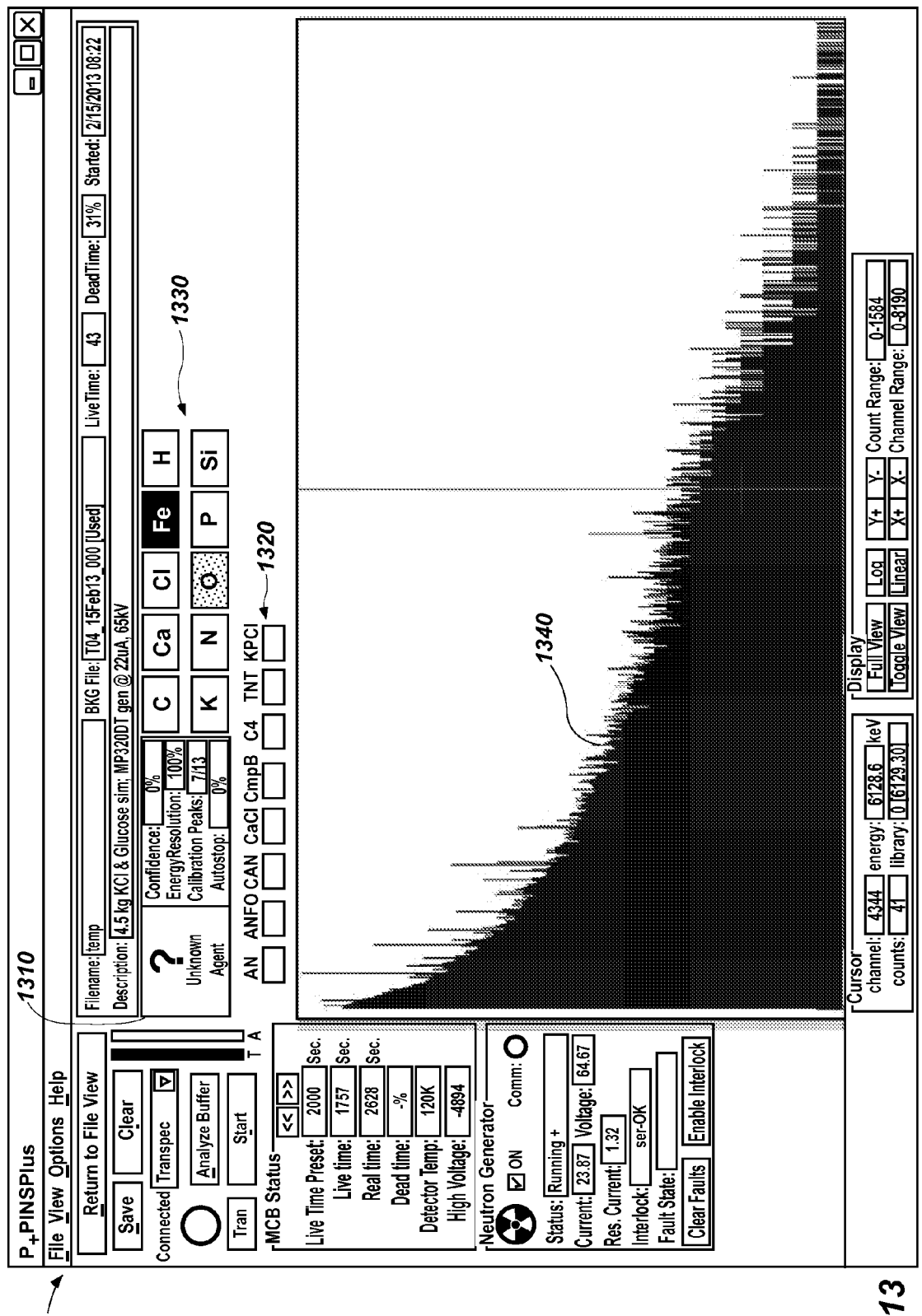
FIG. 13 illustrates a GUI that may be displayed to show substantially real-time information about the progress of a test early in the test, present state of the gamma-ray spectrum, and present confidence levels for the presence of various chemical elements and compounds.

FIG. 13 illustrates a GUI 1300 that may be displayed to show substantially real-time information about progress of a test early in the test, present state of the gamma-ray spectrum 1340, and present confidence levels for the presence of various chemical elements and compounds. The region on the left side of the GUI was explained above with reference to FIGS. 12A-12C.

A region in the upper right corner of the GUI shows a "Live Time" indicator. In FIG. 13 this indicator shows 43 indicating that it is very early in the present test.

Element indicator and browse buttons 1330 are displayed for all the elements of interest for the current analysis. A shading of the buttons is included to indicate the confidence that the element has been detected. The darker the color, the more confident that the element is present in the fill. Pressing any of the buttons takes the operator to a spectral view of that element's region of interest in the spectrum. If there is more than one region of interest for any element, pressing the button a second time will move the operator to the second region of interest for that element. In this region, the shading of the elements may change as the test progresses. FIG. 13 illustrates a point in time early in the test cycle. As a result, the button for iron (Fe) shows a mid-level shading indicating a mid-level of confidence that iron is present. The button for oxygen (O) shows a light shading indicating a small confidence that oxygen is present. The other buttons do not show any shading at this point in the test. While described as light, mid-level, and dark for shading, embodiments of the present disclosure may use more gradual and much finer gradients for the shading. In addition, some embodiments may use different colors for different indication of confidence levels.

An analysis result region 1310 is displayed to the left of the element indicator and browse buttons 1330. This region gives information such as what agent (e.g., chemical compound) is presently thought to be present in the suspect object. It may also give information on the confidence level for this agent, then energy resolution for this agent, and calibration peak ratios for this element. The confidence levels, as well as what agent may appear in this region may change as the test progresses. FIG. 13 illustrates a point in time early in the test cycle. As a result, no agent is presently displayed and there is 0% confidence at this point.

A current state of the gamma-ray spectrum 1340 is displayed in the primary portion of the display and illustrates the entire range of channels in the spectrum. This display may be updated as the test progresses.

An agent indicator region 1320 is shown below the analysis result region 1310 and the element indicator and browse buttons 1330. This agent indicator region 1320 may use color gradients similar to those for the element indicator and browse buttons 1330 to show a present confidence level that a given agent is present. In this embodiment, the agents that are being analyzed for are: Amatol (AM), Ammonium Nitrate and Fuel Oil (AMFO), Calcium Ammonium Nitrate (CAN), Calcium per Chlorate (CaCl), Composition B (CmpB), C4, TNT, and Potassium per Chlorate (KPCl). FIG. 13 illustrates a point in time early in the test cycle. As a result, no agent is presently displayed with any confidence level at this point.

Below the gamma-ray spectrum 1340 is a region showing information and controls for the display in the central region where the gamma-ray spectrum 1340 is currently displays. A "Toggle View" button allows the user to toggle between the present view and a bar graph view in the central region as explained below with reference to FIG. 15. There are also buttons to change the x-axis and y-axis between linear and logarithmic presentations and there are also regions to show the present count range (i.e., the y-axis) and the present channel range (i.e., the x-axis).

FIGS. 14-21 display alternate views of the basic GUI shown in FIG. 13. They also present information at different points in time of the test. Therefore, for ease of description element numbers are not presented on these figures unless needed to distinguish from the element numbers of FIG. 13.

Figure 14:
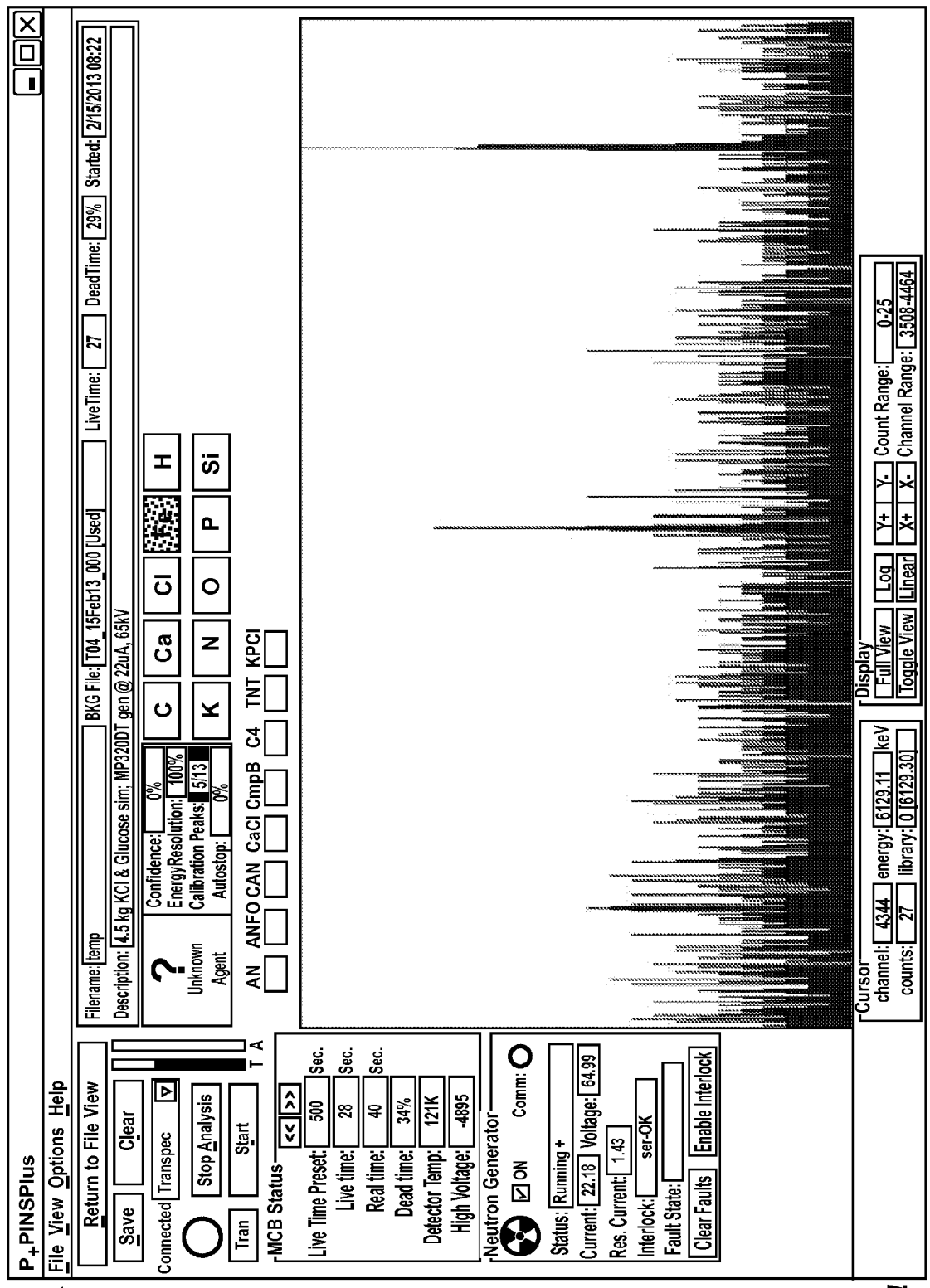
FIG. 14 illustrates a GUI similar to FIG. 13 showing progress early in the test and with the gamma-ray spectrum zoomed in on a region of interest for detecting oxygen.

FIG. 14 illustrates a GUI 1400 similar to FIG. 13 showing progress early in the test and with the gamma-ray spectrum zoomed in on a region of interest for detecting oxygen. This display would result from the user pressing the oxygen button from the element indicator and browse buttons 1330. Note that the "Live Time" indicator shows 27 indicating that it is very early in the present test. The channel range indicator at the bottom of the GUI 1400 shows a range of 3508 to 4464, which is a range where oxygen would be expected to show peaks in the gamma-ray spectrum 1340.

Figure 15:
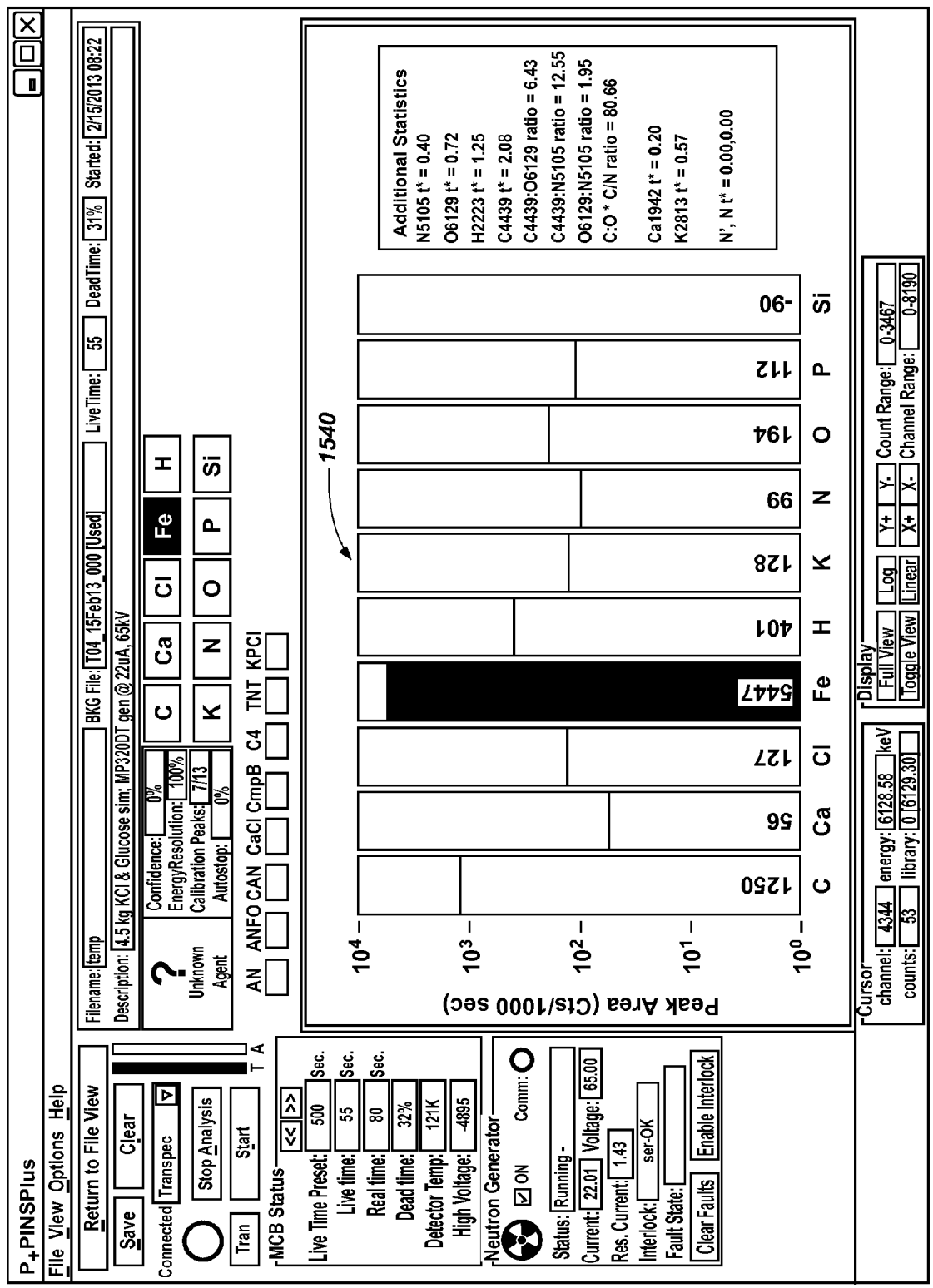
FIG. 15 illustrates a GUI similar to FIG. 13 showing progress early in the test and showing bar graphs of confidence levels for various chemical elements rather than the gamma-ray spectrum.

FIG. 15 illustrates a GUI 1500 similar to FIG. 13 showing progress early in the test and showing bar graphs 1540 of confidence levels for various chemical elements rather than the gamma-ray spectrum 1340. These bar graphs 1540 show information similar to that of the element indicator and browse buttons 1330 but also show current count levels and levels that would need to be achieved for a high confidence that the chemical element is present. Note that the "Live Time" indicator shows 55 indicating that it is very early in the present test. In FIG. 15, the only bar graph that shows a high confidence level is for iron.

Figure 16:
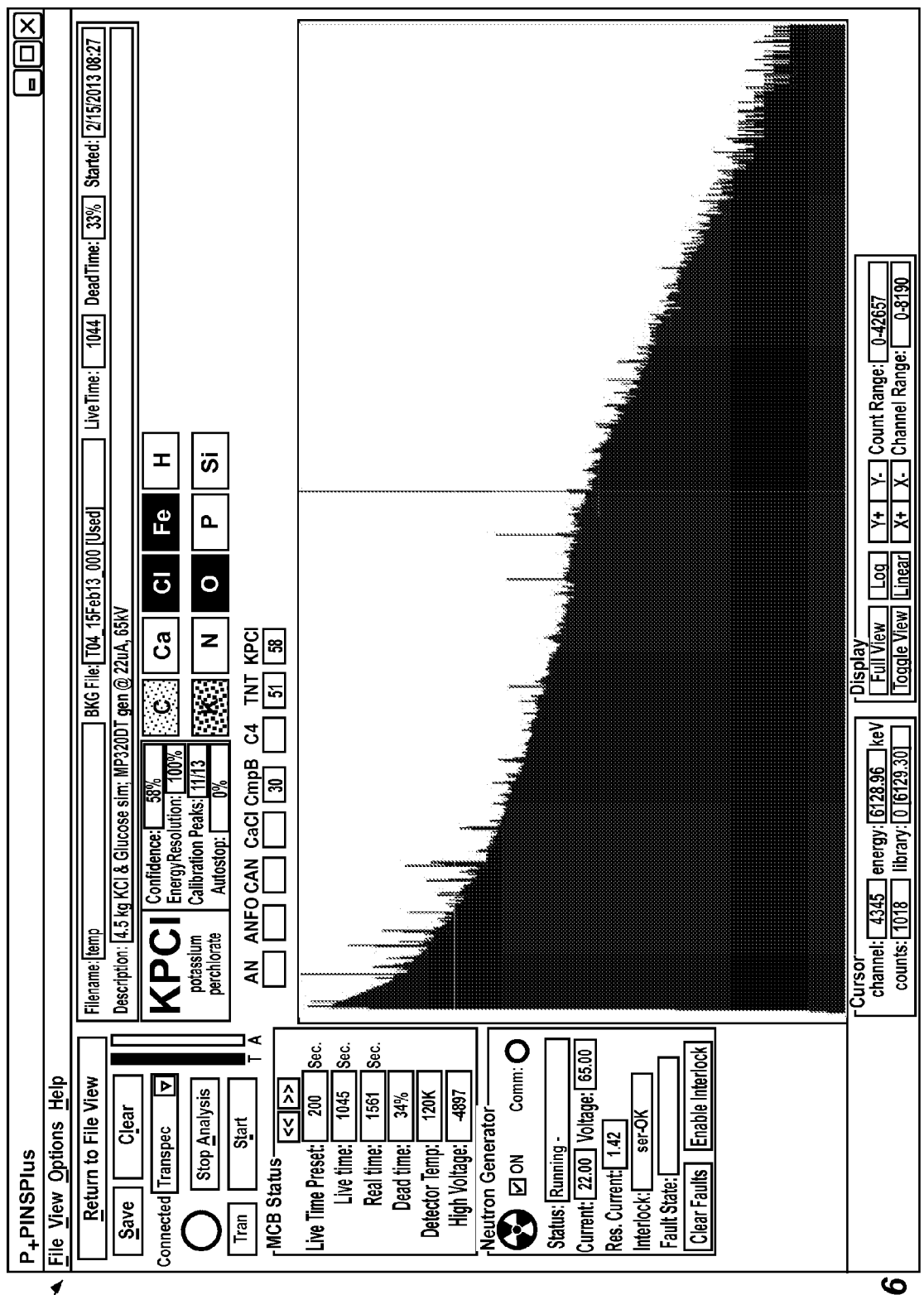
FIG. 16 illustrates a GUI similar to FIG. 13 showing progress midway through the test and with the full gamma-ray spectrum.

FIG. 16 illustrates a GUI 1600 similar to FIG. 13 showing progress midway through the test and with the full gamma-ray spectrum. Note that the "Live Time" indicator shows 1044 indicating that the process is in the mid-range of the present test. In FIG. 16, in comparison to FIG. 13, it can be seen that now the analysis result region indicates that potassium per chlorate may be present with a confidence level of about 53%. Also in FIG. 16, in comparison to FIG.

13, it can be seen that now the element indicator and browse buttons 1320 indicate a high likelihood for the presence of iron, chlorine, and oxygen. A mid-level confidence is indicated for potassium and a lower level confidence is indicated for carbon. Also note that the agent indicator region 1320 now shows a 58% confidence level for potassium per chlorate, a 30% confidence level for CmpB, and a 51% confidence level for TNT.

Figure 17:
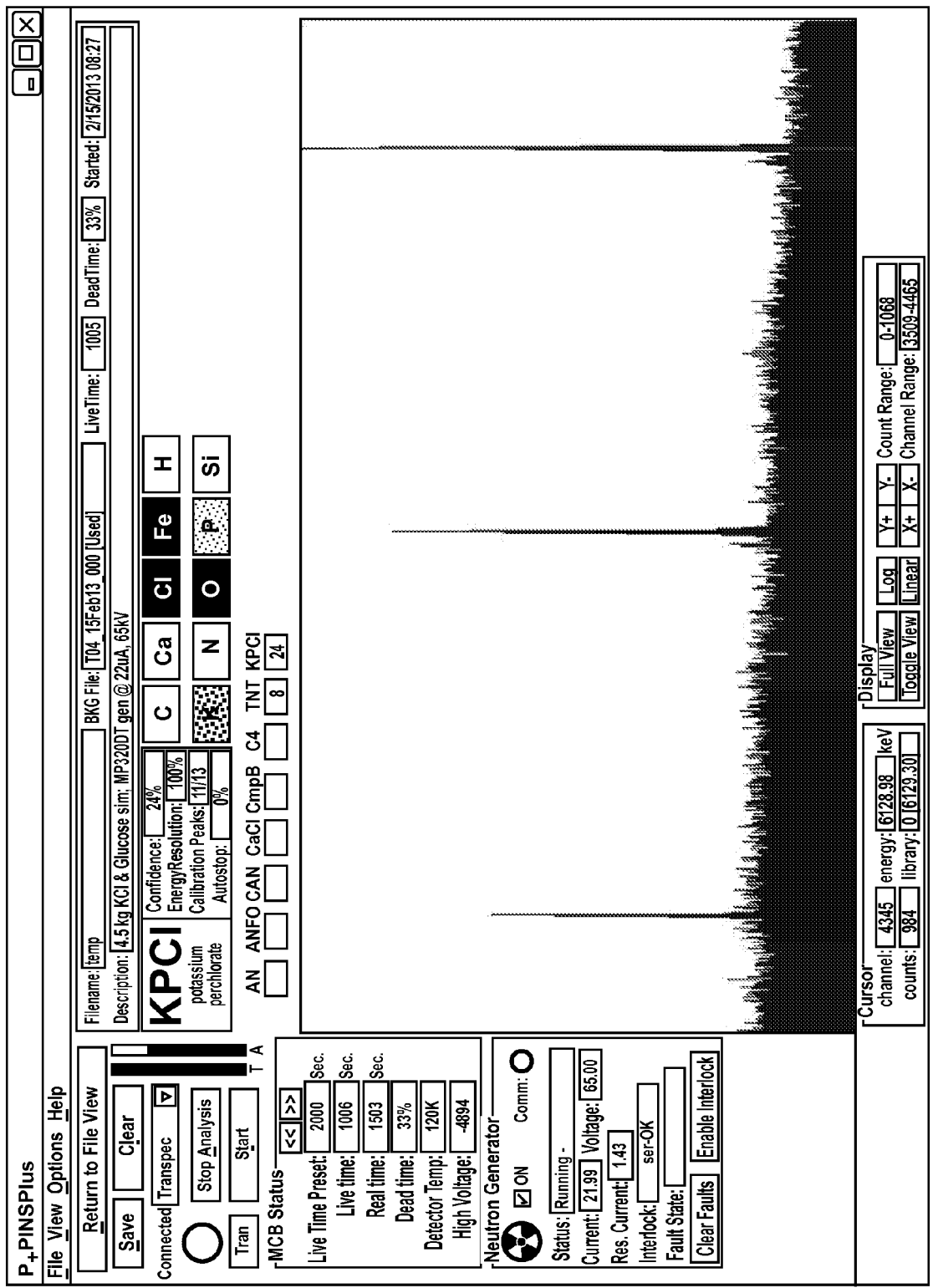
FIG. 17 illustrates a GUI similar to FIG. 13 showing progress midway through the test and with the gamma-ray spectrum zoomed in on a region of interest for detecting oxygen.

FIG. 17 illustrates a GUI 1700 similar to FIG. 13 showing progress midway through the test and with the gamma-ray spectrum zoomed in on a region of interest for detecting oxygen. Note that the "Live Time" indicator shows 1005 indicating that the process is in the mid-range of the present test. In FIG. 17, in comparison to FIG. 14, it can be seen that now the gamma-ray spectrum 1340 shows large well-defined peaks, which indicates a high confidence that oxygen is present.

Figure 18:
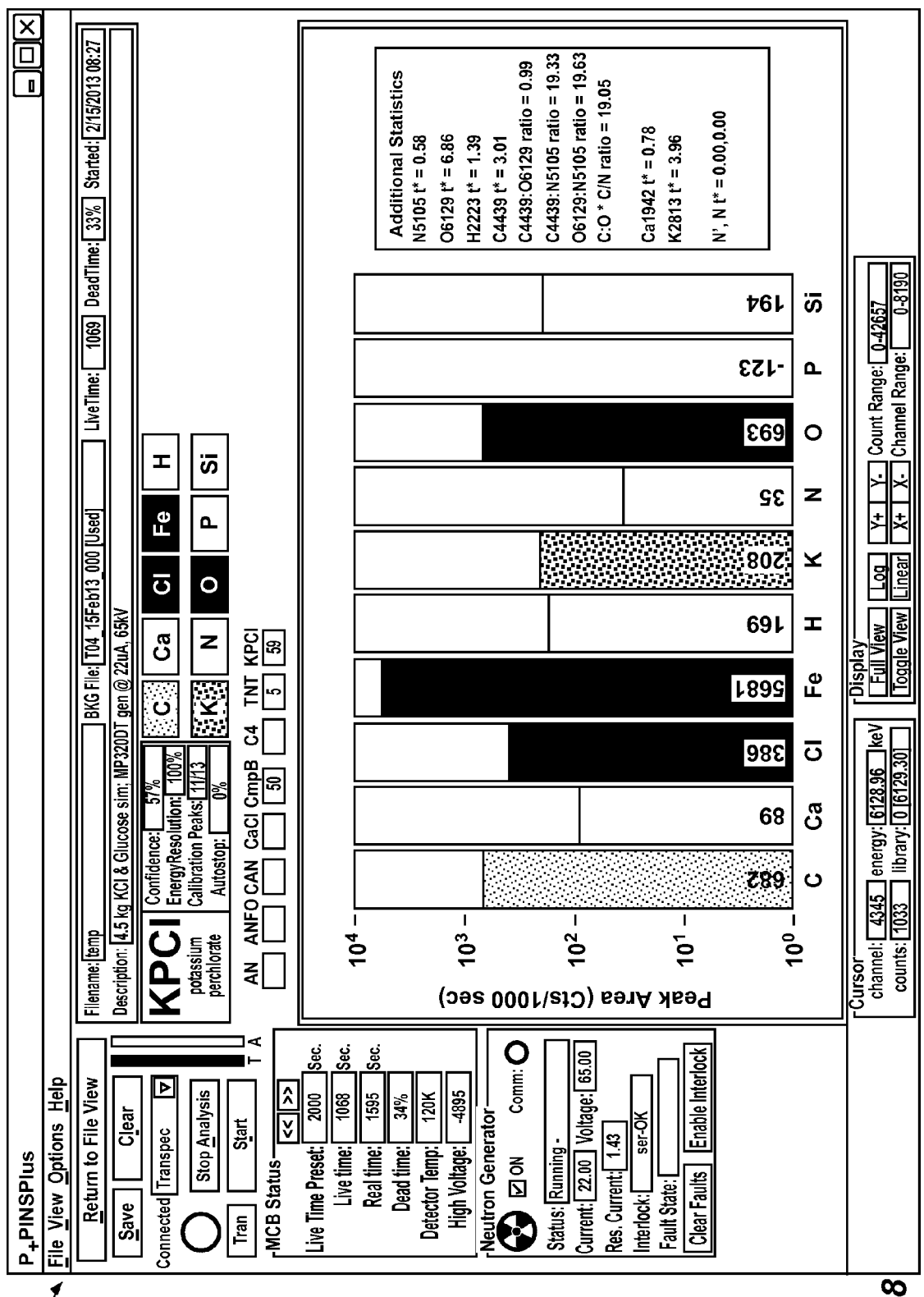
FIG. 18 illustrates a GUI similar to FIG. 13 showing progress midway through the test and showing bar graphs of confidence levels for various chemical elements rather than the gamma-ray spectrum.

FIG. 18 illustrates a GUI 1800 similar to FIG. 13 showing progress midway through the test and showing bar graphs of confidence levels for various chemical elements rather than the gamma-ray spectrum. Note that the "Live Time" indicator shows 1069 indicating that the process is in the mid-range of the present test. In FIG. 18, in comparison to FIG. 15, it can be seen that now the bar graphs 1540 indicate a high likelihood for the presence of iron, chlorine, and oxygen. A mid-level confidence is indicated for potassium and a lower level confidence is indicated for carbon. Note that the shading indications in the bar graphs 1540 are similar to those for the element indicator and browse buttons 1330.

Figure 19:
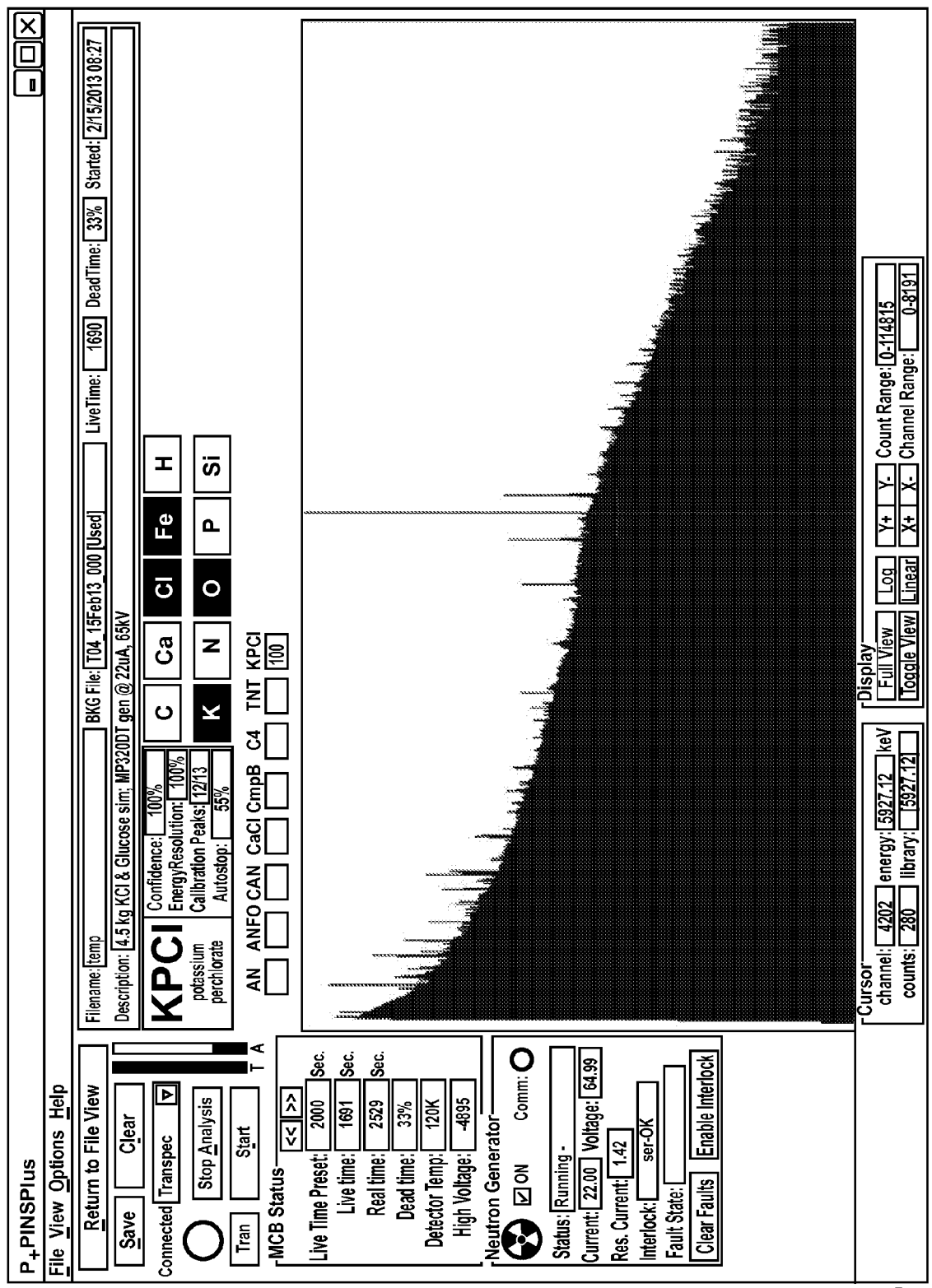
FIG. 19 illustrates a GUI similar to FIG. 13 showing progress late in the test and with the full gamma-ray spectrum.

FIG. 19 illustrates a GUI 1900 similar to FIG. 13 showing progress late in the test and with the full gamma-ray spectrum. Note that the "Live Time" indicator shows 1690 indicating that the process is in the late stage of the present test. In FIG. 19, in comparison to FIG. 16, it can be seen that now the analysis result region indicates that potassium per chlorate may be present with a confidence level of about 100%. Also in FIG. 19, in comparison to FIG. 16, it can be seen that now the element indicator and browse buttons 1320 indicate a high likelihood for the presence of iron, chlorine, oxygen and potassium. Note that the confidence level for the presence of carbon has now gone down relative to the mid-range time period illustrated in FIG. 16. Also note that the agent indicator region 1320 now shows a 100% confidence level for potassium per chlorate, and the confidence levels for CmpB, and TNT have returned to zero.

Figure 20:
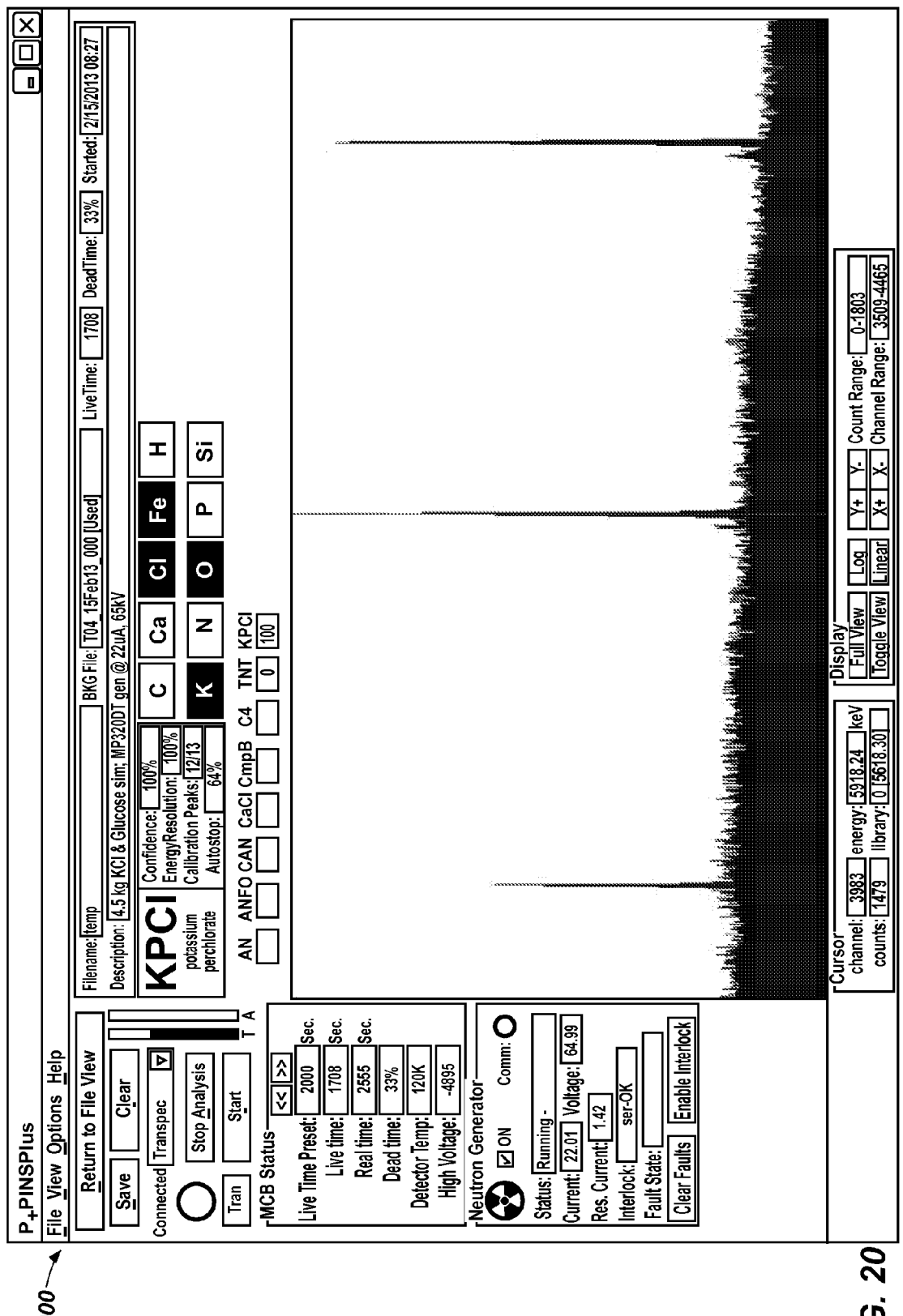
FIG. 20 illustrates a GUI similar to FIG. 13 showing progress late in the test and with the gamma-ray spectrum zoomed in on a region of interest for detecting oxygen.

FIG. 20 illustrates a GUI 2000 similar to FIG. 13 showing progress late in the test and with the gamma-ray spectrum zoomed in on a region of interest for detecting oxygen. Note that the "Live Time" indicator shows 1708 indicating that the process is in the late stage of the present test. FIG. 20 in the late stage is very similar to FIG. 17 in the mid-range stage because oxygen was well identified in the mid-range stage and that has not changed significantly in the late stage except that the peaks are much more pronounced as indicated by the y-axis covering 0 to 1068 counts in FIG. 17 and 0-1803 counts in FIG. 20.

Figure 21:
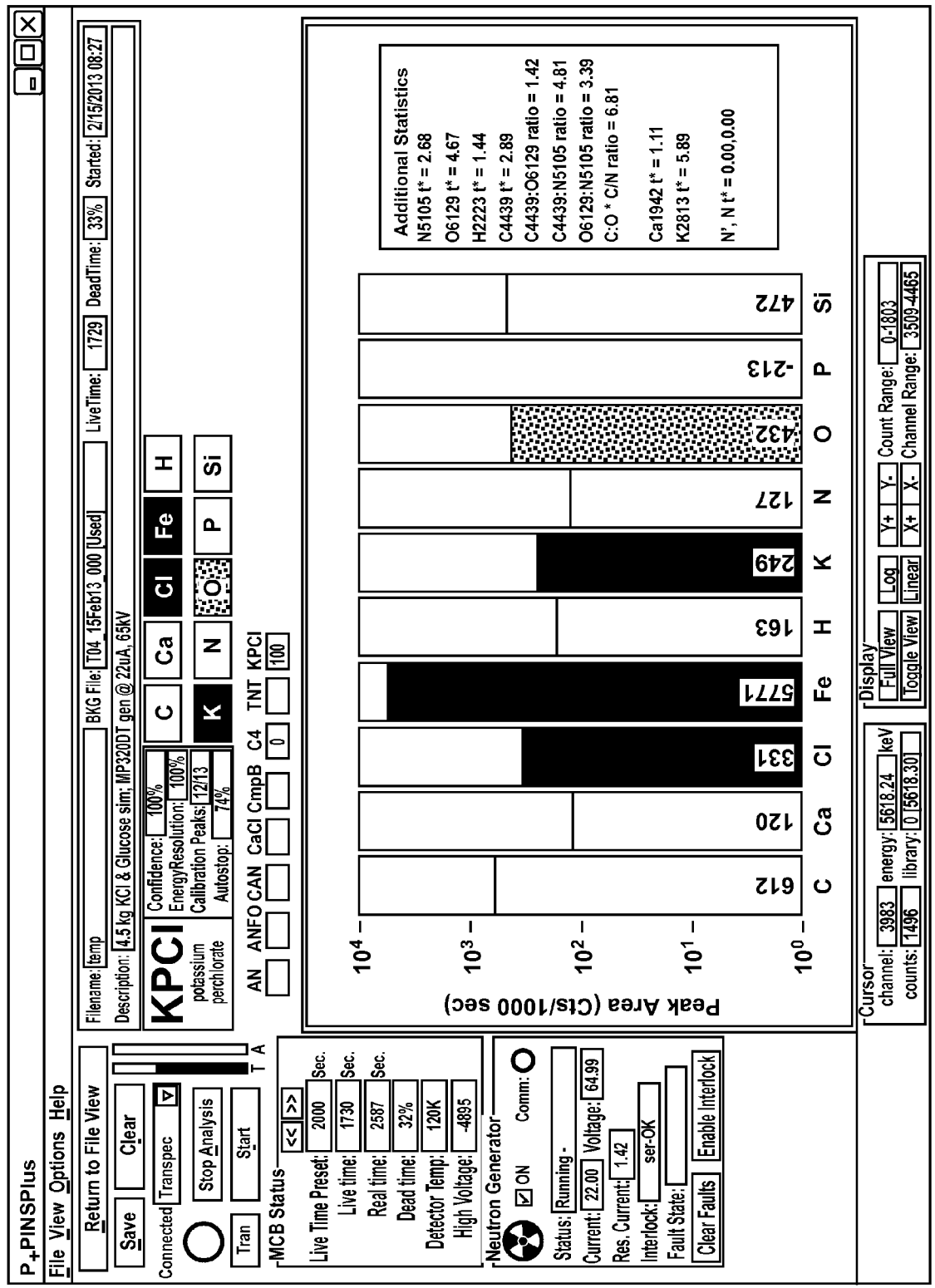
FIG. 21 illustrates a GUI similar to FIG. 13 showing progress late in the test and showing bar graphs of confidence levels for various chemical elements rather than the gamma-ray spectrum.

FIG. 21 illustrates a GUI 2100 similar to FIG. 13 showing progress late in the test and showing bar graphs of confidence levels for various chemical elements rather than the gamma-ray spectrum. Note that the "Live Time" indicator shows 1729 indicating that the process is in the late stage of the present test. In FIG. 21, in comparison to FIG. 18, it can be seen that now the bar graphs 1540 indicate a high likelihood for the presence of iron, chlorine, oxygen and potassium. Note that the confidence level for the presence of carbon has now gone down relative to the mid-range time period illustrated in FIG. 18.

Figure 22:
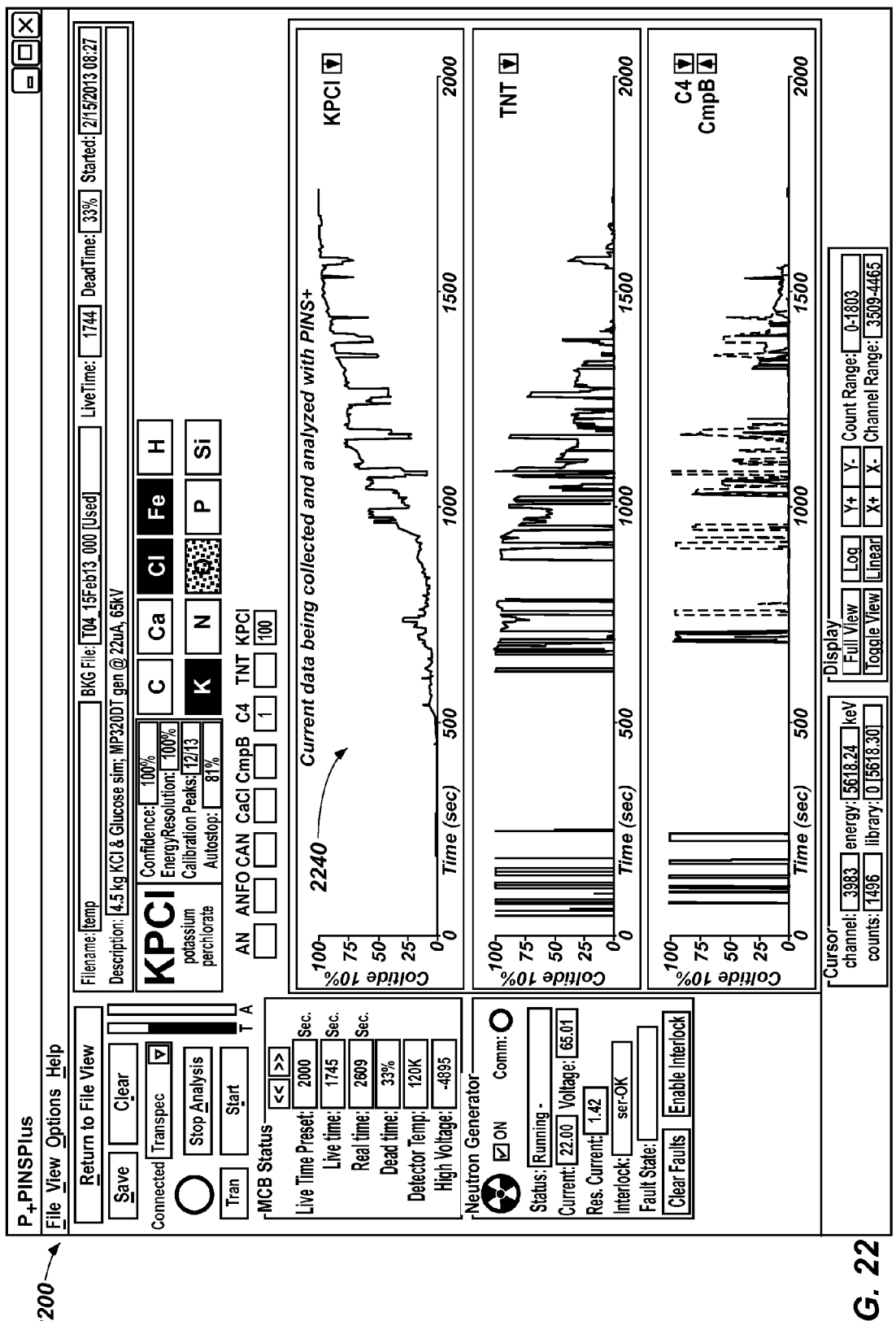
FIG. 22 illustrates identification confidence level graphs for three possible fill chemicals in the central region of the GUI.

FIG. 22 illustrates identification confidence level graphs for three possible fill chemicals in the central region of the GUI 2200. These timeline graphs 2240 show the change in confidence levels for the agents KPCl, TNT and C4. As can be seen, early in the test, there were some indications that TNT may be present, and some indications that C4 may be present. As time in the test passes, and more counts are developed, that algorithms for determining presence of the various agents gradually settle on a very high confidence for the presence of KPCl and a very low confidence for TNT and C4.

In some embodiments, during data acquisition, the analysis of the gamma-ray spectrum and confidence levels for agents and chemical elements may be configured to be complete and updated about every 2-10 seconds. This update process gives the operator a substantially real-time view of the progress of the analysis. As a result, if progress rapidly identifies a particular agent of interest, the operator may be able to save time by stopping the data acquisition at that point, rather than waiting for the entire data acquisition cycle to complete.

While the present disclosure may be susceptible to various modifications and alternative forms, specific embodiments have been shown by way of example in the drawings and have been described in detail herein; however, it should be understood that the disclosure is not intended to be limited to the particular forms disclosed. Rather, the disclosure includes all modifications, equivalents, legal equivalents, and alternatives falling within the scope of the disclosure as defined by the following appended claims.

What is claimed is:

1. A chemical detection system, comprising:
a frame;
an emitter coupled to the frame and configured to direct neutrons at an object to be tested that is positioned external to the frame;
a detector coupled to the frame proximate the emitter; and
a shielding system coupled to the frame and positioned at least partially between the emitter and the detector, the shielding system comprising a moderator block comprising a thermoplastic material and partially surrounding the emitter, the moderator block configured to alter fast neutrons emitted by the emitter in a direction away from the object to one of slow neutrons or thermal neutrons and to redirect the one of the slow neutrons or the thermal neutrons back toward the object to be tested, the moderator block comprising an opening configured to provide at least some fast neutrons emitted by the emitter in a direction toward the object a direct path of travel to the object to be tested, wherein the emitter, the detector, and the shielding system are each positioned within and encompassed by the frame, wherein the frame positions a sensing surface of the detector in a direction substantially parallel to a plane positioned external to the frame and extending along a front portion of the frame, wherein the frame positions the emitter and the shielding system to each extend along the plane, wherein the emitter, the detector, and the shielding system are positioned in a linear row extending parallel to the plane, and wherein the frame orients a centerline of the sensing surface of the detector and a slot of the emitter to be a same distance from a base of the frame.

2. The chemical detection system of claim 1, wherein the frame positions the sensing surface of the detector directly parallel to the plane extending along the front portion of the frame.

3. The chemical detection system of claim 1, wherein the frame comprises a detector bracket mounting the detector to the frame and an emitter bracket mounting the emitter to the frame, the detector bracket and the emitter bracket sized and positioned to orient the detector and the emitter along the plane, and the detector bracket comprises a portion mounting at least a portion of the shielding system to the frame.

4. The chemical detection system of claim 1, wherein the shielding system comprises at least one block comprising a metal material.

5. The chemical detection system of claim 1, wherein the shielding system comprises a collimator surrounding a nose portion of the detector.

6. The chemical detection system of claim 1, further comprising a mechanical cooling system in thermally conductive proximity to the detector.

7. The chemical detection system of claim 6, wherein the mechanical cooling system comprises a Stirling-cycle refrigerator.

8. A method of detecting a chemical makeup of an object with a portable chemical detection system, the method comprising:
   emitting neutrons at the object with a neutron emitter of the portable chemical detection system, the emitting comprising:
      altering, with a moderator block partially surrounding the emitter, fast neutrons emitted by the emitter in a direction away from the object to one of slow neutrons or thermal neutrons;
      redirecting, with the moderating block, the one of the slow neutrons or the thermal neutrons back toward the object; and
      directing at least some fast neutrons emitted by the emitter along a direct path of travel to the object extending at least partially through an opening formed in the moderator block partially surrounding the emitter;
   detecting radiation generated by the object responsive to excitation of at least a portion of the object by the neutrons from the neutron emitter with a detector of the portable chemical detection system, wherein each of the neutron emitter and the detector of the portable chemical detection system are positioned along a single plane extending through the portable chemical detection system; and
   moving the portable chemical detection system along at least a portion of the object, wherein the portable chemical detection system is moved along the at least a portion of the object in another plane parallel to the single plane.

9. The method of claim 8, further comprising mechanically cooling the detector with a Stirling-cycle refrigerator.

10. A chemical analysis system, comprising:
   a neutron generator configured for directing neutrons at a suspect object;
   a moderator block partially surrounding the neutron generator, the moderator block comprising an opening configured to provide at least some fast neutrons emitted by the neutron generator in a direction toward the suspect object a direct path of travel to the suspect object, the system configured to:
      alter, with the moderator block, at least some fast neutrons emitted by the neutron generator in a direction away from the suspect object to one of slow neutrons or thermal neutrons;
      redirect, with the moderating block, at least some of the one of the slow neutrons or the thermal neutrons back toward the suspect object and
      direct at least some fast neutrons emitted by the neutron generator along the direct path of travel to the suspect object through the opening formed in the moderator block;
   a gamma-ray spectrometer configured for detecting gamma rays emitted from the suspect object and communicating spectrometer information regarding the detected gamma rays;
   a computing system configured for operable communication with the gamma-ray spectrometer to receive the spectrometer information, the computing system comprising;
      a memory configured for storing computing instructions; and
      a processor operably coupled to the memory and configured for executing the computing instructions to:
         present a Graphical User Interface (GUI) with dynamic status of an ongoing neutron spectroscopy process, wherein the dynamic status includes a present confidence for a plurality of compounds being present in the suspect object.

11. The chemical analysis system of claim 10, wherein the processor is further configured to display the dynamic status to include an indication that a specific compound of the plurality of compounds has been identified with a high probability level.

12. The chemical analysis system of claim 10, wherein the processor is further configured to display the dynamic status to include a present confidence for a plurality of chemical elements related to the plurality of compounds.

13. The chemical analysis system of claim 10, wherein the processor is further configured to display the dynamic status to include a gamma-ray spectrum of a full channel range that is dynamically updated as the neutron spectroscopy process progresses.

14. The chemical analysis system of claim 10, wherein the processor is further configured to display the dynamic status to include a gamma-ray spectrum of a limited channel range related to a particular chemical element that is dynamically updated as the neutron spectroscopy process progresses.

15. The chemical analysis system of claim 10, wherein the processor is further configured to display the dynamic status to include bar graphs for a plurality of chemical elements indicating a present count level and a confidence level for each chemical element of the plurality of chemical elements.

16. The chemical analysis system of claim 10, wherein the processor is further configured to display the dynamic status to include a timeline of a confidence level for at least one compound of the plurality of compounds as the neutron spectroscopy process progresses.

17. The chemical analysis system of claim 10, wherein the dynamic status of the present confidence is indicated as a gradient shading to indicate a confidence level between zero percent and one hundred percent.

18. A method of analyzing composition of a suspect object, comprising:
   positioning the chemical analysis system of claim 10 proximate a suspect object;
   directing neutrons at the suspect object with the neutron generator;
   detecting gamma rays emitted from the suspect object with the gamma-ray spectrometer;

communicating spectrometer information regarding the detected gamma rays with the computing system; and presenting a dynamic status of an ongoing neutron spectroscopy process to a user with the GUI.

19. The method of claim 18, wherein the GUI further includes a region to display a present confidence for a plurality of chemical elements related to the at least one of the plurality of compounds.

20. The method of claim 18, wherein the GUI further includes a region to display a present confidence for a plurality of chemical elements related to the plurality of compounds.

21. The method of claim 18 wherein the GUI further includes a region to display a gamma-ray spectrum of a full channel range that is dynamically updated as the neutron spectroscopy process progresses.

22. The method of claim 18, wherein the GUI further includes a region to display a gamma-ray spectrum of a limited channel range related to a particular chemical element that is dynamically updated as the neutron spectroscopy process progresses.

23. The method of claim 18, wherein the GUI further includes a region to display the dynamic status to include bar graphs for a plurality of chemical elements indicating a present count level and a confidence level for each chemical element of the plurality of chemical elements.

24. The method of claim 18, wherein the GUI further includes a region to display a timeline of a confidence level for at least one compound of the plurality of compounds as the neutron spectroscopy process progresses.

25. The method of claim 18, wherein the GUI further includes a region to display an indication that a specific compound of the plurality of compounds has been identified with a high probability level.

26. A chemical detection system, comprising:

a frame;

an emitter coupled within the frame and configured to direct neutrons at an object to be tested that is positioned external to the frame;

a detector coupled within the frame proximate the emitter, the detector comprising a crystal configured to detect radiation emitted from the object to be tested; and a shielding system coupled within the frame and positioned at least partially between the emitter and the detector, the shielding system comprising a moderator block comprising a thermoplastic material and partially surrounding the emitter, each of a sensing surface of the detector, the emitter, and the shielding system being linearly positioned within the frame along an axis extending along a front portion of the frame, wherein the frame positions the shielding system between the detector and the emitter such that neutrons generated by the emitter do not have a direct path to the crystal within the detector wherein the moderator block comprises an opening configured to provide at least some fast neutrons emitted by the emitter in a direction toward the object a direct path of travel to the object to be tested, and wherein the frame orients a centerline of the crystal of the detector and an output of the emitter to be a same distance from a base of the frame.

* * * * *

UNITED STATES PATENT AND TRADEMARK OFFICE
CERTIFICATE OF CORRECTION

PATENT NO.       : 9,689,814 B2
APPLICATION NO.  : 13/847266
DATED            : June 27, 2017
INVENTOR(S)      : Augustine J. Caffrey et al.

It is certified that error appears in the above-identified patent and that said Letters Patent is hereby corrected as shown below:

In the Specification

| | | |
|---|---|---|
| Column 10, | Lines 29, 30, | change "(compact disks), discs)," to --(compact discs),-- |
| Column 11, | Line 53, | change "gamma ray gamma-ray" to --gamma-ray-- |
| Column 18, | Lines 5, 6, | change "of the GUI 2200" to --of GUI 2200-- |

In the Claims

| | | | |
|---|---|---|---|
| Claim 26, | Column 22, | Line 24, | change "within the detector wherein" to --within the detector, wherein-- |

Signed and Sealed this
Twenty-seventh Day of February, 2018

Andrei Iancu
*Director of the United States Patent and Trademark Office*